US005858535A

United States Patent [19]

Wang et al.

[11] Patent Number: 5,858,535
[45] Date of Patent: Jan. 12, 1999

[54] ABSORBENT ARTICLES COMPRISING ABSORBENT MEMBERS COMPRISING ABSORBENT MATERIALS HAVING IMPROVED ABSORBENT PROPERTY

[75] Inventors: Lin Wang; Ebrahim Rezai; Yumiko Hayashi, all of Kobe, Japan

[73] Assignee: The Procter & Gamble Company, Cincinnati, Ohio

[21] Appl. No.: 126,679

[22] Filed: Jul. 30, 1998

Related U.S. Application Data

[62] Division of Ser. No. 779,727, Jan. 6, 1997, which is a continuation of Ser. No. 298,886, Aug. 31, 1994, abandoned, which is a continuation-in-part of Ser. No. 197,913, Feb. 17, 1994, abandoned.

[51] Int. Cl.$^6$ ..................................................... B32B 5/16
[52] U.S. Cl. ......................... 428/407; 428/913; 604/367; 604/368; 604/372
[58] Field of Search ........................... 428/407; 604/367, 604/368, 372

[56] References Cited

U.S. PATENT DOCUMENTS

| | | | |
|---|---|---|---|
| Re. 32,649 | 4/1988 | Brandt et al. ............................ 604/368 |
| 2,926,116 | 2/1960 | Keim ....................................... 162/164 |
| 2,926,154 | 2/1960 | Keim ....................................... 260/29.2 |
| 3,332,901 | 7/1967 | Keim ....................................... 260/29.2 |
| 3,661,875 | 5/1972 | Sieja ........................................ 260/85.5 |
| 3,758,641 | 9/1973 | Zweigle .................................... 260/874 |
| 4,062,817 | 12/1977 | Westerman ............................ 260/17.45 |
| 4,076,663 | 2/1978 | Masuda et al. ........................ 260/17.4 |
| 4,076,673 | 2/1978 | Burkholder, Jr. ...................... 260/29.6 |
| 4,093,776 | 6/1978 | Aoki et al. ............................. 428/402 |
| 4,132,695 | 1/1979 | Burkholder ............................ 260/29.2 |
| 4,154,898 | 5/1979 | Burkholder, Jr. ...................... 428/500 |
| 4,190,563 | 2/1980 | Bosley et al. .......................... 260/17.4 |
| 4,310,593 | 1/1982 | Gross ...................................... 428/290 |
| 4,333,461 | 6/1982 | Muller .................................... 128/284 |
| 4,340,706 | 7/1982 | Obayashi et al. ....................... 526/207 |
| 4,413,995 | 11/1983 | Korpman ................................ 604/368 |
| 4,446,261 | 5/1984 | Yamasaki et al. ...................... 524/40 |
| 4,474,949 | 10/1984 | Chatterjee et al. ...................... 536/56 |
| 4,506,052 | 3/1985 | Furukawa et al. ...................... 524/357 |
| 4,541,871 | 9/1985 | Obayashi et al. ...................... 106/197.2 |
| 4,587,308 | 5/1986 | Makita et al. .......................... 525/373 |
| 4,605,401 | 8/1986 | Chmelir et al. ........................ 604/368 |
| 4,624,868 | 11/1986 | Muller .................................... 427/384 |
| 4,625,001 | 11/1986 | Tsubakimoto et al. ................. 526/88 |
| 4,647,617 | 3/1987 | Saotome ................................. 524/733 |
| 4,654,039 | 3/1987 | Brandt et al. .......................... 604/368 |
| 4,666,983 | 5/1987 | Tsubakimoto et al. ................. 525/119 |
| 4,677,174 | 6/1987 | Alexander et al. .................... 526/240 |
| 4,690,971 | 9/1987 | Flesher et al. ......................... 524/555 |
| 4,693,713 | 9/1987 | Chmelir et al. ........................ 604/368 |
| 4,698,404 | 10/1987 | Cramm et al. ......................... 526/204 |
| 4,715,918 | 12/1987 | Lang ....................................... 156/273.1 |
| 4,734,478 | 3/1988 | Tsubakimoto et al. ................. 527/300 |
| 4,735,987 | 4/1988 | Morita et al. .......................... 524/436 |
| 4,755,562 | 7/1988 | Alexander et al. .................... 525/113 |
| 4,758,617 | 7/1988 | Tanioku et al. ........................ 524/413 |
| 4,766,173 | 8/1988 | Bailey et al. ........................... 524/819 |
| 4,777,200 | 10/1988 | Dymond et al. ....................... 524/458 |
| 4,783,510 | 11/1988 | Saotome ................................. 525/329.7 |
| 4,798,861 | 1/1989 | Johnson ................................... 524/458 |
| 4,820,773 | 4/1989 | Alexander et al. .................... 525/274 |
| 4,824,901 | 4/1989 | Alexander et al. .................... 524/555 |
| 4,833,179 | 5/1989 | Young et al. .......................... 522/183 |
| 4,861,539 | 8/1989 | Allen et al. ............................ 264/204 |
| 4,880,858 | 11/1989 | Farrar et al. ........................... 524/60 |
| 4,921,904 | 5/1990 | Sparapany et al. ................... 525/929.9 |
| 4,950,692 | 8/1990 | Lewis et al. ........................... 521/45 |
| 4,954,562 | 9/1990 | Anderson ............................... 524/779 |
| 4,962,172 | 10/1990 | Allen et al. ............................ 526/318.42 |
| 4,970,267 | 11/1990 | Bailey et al. ........................... 525/344 |
| 4,973,632 | 11/1990 | Nagasuna et al. ..................... 526/200 |
| 4,980,434 | 12/1990 | Farrar et al. ........................... 526/240 |
| 4,997,714 | 3/1991 | Farrar et al. ........................... 428/394 |

(List continued on next page.)

FOREIGN PATENT DOCUMENTS

| | | | |
|---|---|---|---|
| 159371 | 10/1985 | European Pat. Off. ........ A61L 15/00 |
| 317106 | 5/1989 | European Pat. Off. ........... C08J 3/06 |
| 349241 | 1/1990 | European Pat. Off. .......... C08F 2/32 |
| 450922 | 10/1991 | European Pat. Off. .......... C08F 8/14 |
| 450923 | 10/1991 | European Pat. Off. .......... C08F 8/14 |
| 450924 | 10/1991 | European Pat. Off. .......... C08F 8/14 |
| 493011 | 1/1992 | European Pat. Off. ........ A61L 15/60 |
| 509708 | 10/1992 | European Pat. Off. . |
| 522570 | 1/1993 | European Pat. Off. ........ A61L 15/00 |
| 530438 | 3/1993 | European Pat. Off. ...... C08F 220/06 |
| 547847 | 6/1993 | European Pat. Off. ........ C08F 20/06 |
| 559476 | 9/1993 | European Pat. Off. ...... C08F 220/04 |
| 4020780 | 8/1991 | Germany . |
| 62-112655 | 5/1987 | Japan ................................ C08L 101/00 |
| 63-19215 | 4/1988 | Japan . |
| 1-304127 | 12/1989 | Japan ................................ C08J 3/00 |
| 1-304128 | 12/1989 | Japan ............................. B29B 13/06 |
| 2-30336 | 7/1990 | Japan ................................ C08J 3/12 |
| 2-233139 | 9/1990 | Japan ............................. A61F 13/46 |
| 4-161431 | 6/1992 | Japan ............................. B01D 15/00 |
| 6-370 | 1/1994 | Japan . |
| WO 90/08789 | 8/1990 | WIPO ............................ C08F 265/02 |
| WO 91/15177 | 10/1991 | WIPO ............................ A16F 13/15 |
| WO 91/15362 | 10/1991 | WIPO ............................ B32B 3/10 |
| WO 91/15368 | 10/1991 | WIPO ............................ B32B 31/30 |
| WO 92/16565 | 10/1992 | WIPO ............................ C08F 2/18 |
| WO 93/05080 | 3/1993 | WIPO ............................ A61L 15/24 |

Primary Examiner—Helen L. Pezzuto
Attorney, Agent, or Firm—Carl J. Roof; E. Kelly Linman; Jacobus C. Rasser

[57] ABSTRACT

An absorbent member comprising at least one region which comprises an absorbent material in a concentration of from about 60 to 100% by weight. The absorbent material has a improved physical property after swelling and comprises a mixture of (1) a plurality of absorbent gelling particles comprising a water-insoluble, water-swellable polymer, and (2) an absorbent property modification polymer reactive with at least one component included in a urine. When a urine is applied to the absorbent member, the absorbent gelling particles are spontaneously connective through the absorbent property modification polymer. The absorbent material has at least one of the improved absorbent properties after swelling such as (1) liquid permeability, (2) porosity, (3) wet integrity, and (4) recovery property when subjected to external forces.

28 Claims, 9 Drawing Sheets

U.S. PATENT DOCUMENTS

| | | | |
|---|---|---|---|
| 5,102,597 | 4/1992 | Roe et al. | 264/126 |
| 5,118,719 | 6/1992 | Lind | 521/92 |
| 5,122,544 | 6/1992 | Bailey et al. | 521/40.5 |
| 5,124,188 | 6/1992 | Roe et al. | 428/72 |
| 5,147,956 | 9/1992 | Allen | 526/318.42 |
| 5,149,334 | 9/1992 | Lahrman et al. | 604/367 |
| 5,149,335 | 9/1992 | Kellenberger et al. | 604/372 |
| 5,154,713 | 10/1992 | Lind | 604/358 |
| 5,164,459 | 11/1992 | Kimura et al. | |
| 5,171,781 | 12/1992 | Farrar et al. | 524/547 |
| 5,180,622 | 1/1993 | Berg et al. | 428/192 |
| 5,195,999 | 3/1993 | Harada et al. | 604/368 |
| 5,206,205 | 4/1993 | Tsai | 502/402 |
| 5,236,965 | 8/1993 | Engelhardt et al. | 521/142 |
| 5,250,642 | 10/1993 | Ahmed et al. | 526/240 |
| 5,264,471 | 11/1993 | Chmelir et al. | 524/35 |
| 5,280,079 | 1/1994 | Allen et al. | 525/329.2 |
| 5,286,827 | 2/1994 | Ahmed | 526/287 |
| 5,324,561 | 6/1994 | Razai et al. | 428/72 |
| 5,338,766 | 8/1994 | Phan et al. | 521/63 |
| 5,346,485 | 9/1994 | Yarbrough et al. | 604/368 |
| 5,536,264 | 7/1996 | Hsueh et al. | 604/368 |
| 5,713,881 | 2/1998 | Rezai et al. | 604/368 |

ABSORBENT ARTICLES COMPRISING ABSORBENT MEMBERS COMPRISING ABSORBENT MATERIALS HAVING IMPROVED ABSORBENT PROPERTY

CROSS-REFERENCE TO RELATED APPLICATION

This application is a divisional of copending U.S. application Ser. No. 08/779,727, filed Jan. 6, 1997, allowed, which is a continuation of U.S. application Ser. No. 08/298,886, filed Aug. 31, 1994 (now abandoned), which was a continuation-in-part of U.S. application Ser. No. 08/197,913, filed Feb. 17, 1994 now abandoned.

FIELD OF THE INVENTION

The present invention relates to absorbent members which, upon contacting liquids such as water or body fluids, swell and imbibe such liquids. More specifically, the present invention relates to absorbent members comprising absorbent materials having at least one improved physical property after swelling. The present invention has particular applicability to absorbent articles such as diapers, adult incontinence pads, sanitary napkins, and the like.

BACKGROUND OF THE INVENTION

Water-insoluble, water-swellable, hydrogel-forming absorbent polymers are capable of absorbing large quantities of liquids such as water, body fluids (e.g., urine, blood, menstrual fluid), industrial fluids and household fluids and are further capable of retaining such absorbed liquids under moderate pressures. The absorption characteristics of such polymer materials make them especially useful for incorporation into absorbent articles such as disposable diapers, adult incontinence pads and briefs, and catamenial products such as sanitary napkins, and the like.

The development of highly absorbent members used in such absorbent articles are the subject of substantial commercial interest. A highly desired characteristic for such products is thinness. For example, thinner diapers are less bulky to wear, fit better under clothing, and are less noticeable. They are also more compact in the package, making the diapers easier for the consumer to carry and store. Compactness in packaging also results in reduced distribution costs for the manufacturer and distributor, including less shelf space required in the store per diaper unit.

The ability to provide thinner absorbent articles such as diapers has been contingent on the ability to develop relatively thin absorbent cores or structures that can acquire and store large quantities of discharged body fluids, in particular urine. In this regard, the use of certain absorbent polymers often referred to as "hydrogels," "superabsorbents" or "hydrocolloid" material has been particularly important. See, for example, U.S. Pat. No. 3,699,103 (Harper et al), issued Jun. 13, 1972, and U.S. Pat. No. 3,770,731 (Harmon), issued Jun. 20, 1972, that disclose the use of such absorbent polymers (hereafter "hydrogel-forming absorbent polymers") in absorbent articles. Indeed, the development of thinner diapers has been the direct consequence of thinner absorbent cores that take advantage of the ability of these hydrogel-forming absorbent polymers to absorb large quantities of discharged body fluids, typically when used in combination with a fibrous matrix. See, for example, U.S. Pat. No. 4,673,402 (Weisman et al), issued Jun. 16, 1987 and U.S. Pat. No. 4,935,022 (Lash et al), issued Jun. 19, 1990, that disclose dual-layer core structures comprising a fibrous matrix and hydrogel-forming absorbent polymers useful in fashioning thin, compact, nonbulky diapers.

In the meantime, prior absorbent structures have generally comprised relatively low amounts (e.g., less than about 50% by weight) of these hydrogel-forming absorbent polymers. See, for example, U.S. Pat. No. 4,834,735 (Alemany et al), issued May 30, 1989 (preferably from about 9 to about 50% hydrogel-forming absorbent polymer in the fibrous matrix). There are several reasons for this. The hydrogel-forming absorbent polymers employed in prior absorbent structures have generally not had an absorption rate that would allow them to quickly absorb body fluids, especially in "gush" situations. This has necessitated the inclusion of fibers, typically wood pulp fibers, to serve as temporary reservoirs to hold the discharged fluids until absorbed by the hydrogel-forming absorbent polymer.

More importantly, many of the known hydrogel-forming absorbent polymers exhibited gel blocking when they are used in absorbent articles in a high concentration. "Gel blocking" occurs when particles of the hydrogel-forming absorbent polymer are wetted and the particles swell so as to inhibit fluid transmission to other regions of the absorbent structure. Wetting of these other regions of the absorbent member therefore takes place via a very slow diffusion process. In practical terms, this means acquisition of fluids by the absorbent structure is much slower than the rate at which fluids are discharged, especially in gush situations. Leakage from the absorbent article can take place well before the particles of hydrogel-forming absorbent polymer in the absorbent member are fully saturated or before the fluid can diffuse or wick past the "blocking" particles into the rest of the absorbent member. Gel blocking can be a particularly acute problem if the particles of hydrogel-forming absorbent polymer do not have adequate gel strength and deform or spread under stress once the particles swell with absorbed fluid. See U.S. Pat. No. 4,834,735 (Alemany et al), issued May 30, 1989.

This gel blocking phenomena has typically necessitated the use of a fibrous matrix in which are dispersed the particles of hydrogel-forming absorbent polymer. This fibrous matrix keeps the particles of hydrogel-forming absorbent polymer separated from one another. This fibrous matrix also provides a capillary structure that allows fluid to reach the hydrogel-forming absorbent polymer located in regions remote from the initial fluid discharge point. See U.S. Pat. No. 4,834,735 (Alemany et al), issued May 30, 1989. However, dispersing the hydrogel-forming absorbent polymer in a fibrous matrix at relatively low concentrations in order to minimize or avoid gel blocking may lower the overall fluid storage capacity of thinner absorbent structures. Using lower concentrations of these hydrogel-forming absorbent polymers limits somewhat the real advantage of these materials, namely their ability to absorb and retain large quantities of body fluids per given volume.

In general, increasing the gel strength of hydrogel-forming absorbent polymers can contribute to decrease gel blocking. Gel strength relates to the tendency of the hydrogel formed from these polymers to deform or "flow" under usage stresses. Gel strength needs to be such that the hydrogel formed does not deform and fill to an unacceptable degree the capillary void spaces in the absorbent structure or article, thereby inhibiting the absorbent capacity of the structure/article, as well as the fluid distribution through the structure/article. High gel strength usually obtained by crosslinking. It is believed that crosslinking increases the resistance to deformation of hydrogel-forming absorbent polymer surfaces. However, crosslinking has a deep impact on the absorbent capacity of a hydrogel-forming absorbent polymer. In general, absorbent capacity or "gel volume" has inverse power-law dependence on the level of crosslinking. That is, high crosslinking level results in high gel strength but low gel volume. Gel volume is a measure of the amount of water or body fluids that a given amount of hydrogel-forming polymer can absorb. It is required that gel volume is sufficiently high in order that the hydrogel-forming polymer can absorb significant amounts of the aqueous body fluids encountered during use of the absorbent article.

Another important factor that has to be considered is the liquid permeability of hydrogel-forming absorbent polymers. It has been discovered that the permeability or flow conductivity of the gel layer formed by swelling in the presence of body fluids is extremely important when these absorbent polymers are used in absorbent cores or members at a high concentration in localized or throughout regions thereof. It should be noted that lack of the liquid permeability or flow conductivity of absorbent polymers may directly impact on the ability of resultant gel layers to acquire and distribute body fluids.

Yet another important factor of hydrogel-forming absorbent polymers is the level of extractable polymer material present therein. See U.S. Pat. No. 4,654,039 (Brandt et al), issued Mar. 31, 1987 (reissued Apr. 19, 1988 as Re. 32,649). Many hydrogel-forming absorbent polymers contain significant levels of extractable polymer material. This extractable polymer material can be leached out from the resultant hydrogel by body fluids (e.g., urine) during the time period such body fluids remain in contact with the hydrogel-forming absorbent polymer. It is believed such extracted polymer material can alter both the chemical characteristics (e.g., osmolarity) and physical characteristics (e.g., viscosity) of the body fluid to such an extent that the fluid is more slowly absorbed and more poorly held by the hydrogel. This polymer contaminated fluid is also more poorly transported through the absorbent member. Such a situation can contribute to undesirable and premature leakage of body fluid from the absorbent article. Thus it is desirable to use hydrogel-forming absorbent polymers with lower levels of extractable polymer material.

A further important factor that has to be considered in order to take full advantage of the high concentration of hydrogel-forming absorbent polymers in thinner absorbent articles is the wet integrity of the region or regions in the absorbent member that comprise these polymers. By "good wet integrity" is meant that the region or regions in the absorbent member having the high concentration of hydrogel-forming absorbent polymer have sufficient integrity in a partially wet, and/or wetted state such that the physical continuity of the hydrogel formed after swelling in the presence of body fluids is not substantially disrupted or altered, even when subjected to normal use conditions. During normal use, absorbent cores in absorbent articles are typically subjected to tensional and torsional forces of varying intensity and direction. These tensional and torsional forces include bounching in the crotch area, stretching and twisting forces as the person wearing the absorbent article walks, squats, bends, and the like. If wet integrity is inadequate, these tensional and torsional forces may cause a substantial alternation and/or disruption in the physical continuity of the hydrogel. Such alternation could minimize or completely negate any advantageous fluid distribution (permeability/flow conductivity) property of the hydrogel-forming absorbent polymer. Such alternation and/or disruption may also cause the gel to mobilize and bring about the disclosure of the gel to the surface of absorbent article, therefore cause the so called "gel-on-skin" problem.

Still another important factor of hydrogel-forming absorbent polymers used in thinner absorbent article is the jelly/mushy feel when touching and handling the absorbent article after usage. When hydrogel-forming absorbent polymer is dispersed in region or regions at a high concentration, the swollen gel formed by absorbing body fluids is a gel layer that the particulate is mobile and the gel layer is collapsed when subjected to forces such as pushing, squeezing, etc. when handling the absorbent article after usage. This is why absorbent articles having high concentration of hydrogel-forming absorbent polymer give users or consumers "wet/mushy" feel when touching or handling them from outside.

Therefore, one object of the present invention is to prevent gel blocking phenomena caused in absorbent articles while maintaining required absorbent capacity.

Yet another object of the present invention is to prevent leakage of swollen absorbent materials from absorbent articles.

Still another object of the present invention is to improve the jelly/mushy feel of absorbent articles after usage.

Yet another object of the present invention is to provide thinner absorbent articles.

Still another object of the present invention is to provide thinner absorbent disposable articles such as diapers, sanitary napkins, tampons, and the like.

SUMMARY OF THE INVENTION

Briefly stated, the present invention relates to absorbent members comprising at least one region which comprises an absorbent material, wherein the absorbent material comprises a mixture of (1) a plurality of absorbent gelling particles comprising a water-insoluble, water-swellable polymer, and (2) an absorbent property modification polymer reactive with at least one component included in a urine.

In one aspect of the invention, when the absorbent material swells by absorbing a urine and is formed into a predetermined layer of the swollen absorbent material under a predetermined load, the layer of the swollen absorbent material has a Gel Bulk Density (GBD) value of below 0.95 g/cm$^3$ in the GBD test.

In another aspect of the invention, when the absorbent material swells by absorbing a urine and is formed into a predetermined layer of the swollen absorbent material, the layer of the swollen absorbent material has a Saline Flow Conductivity (SFC) value of at least $20 \times 10^{-7}$ cm$^3$sec/g in the SFC test.

In yet another aspect of the invention, when the absorbent material swells by absorbing a urine and is formed into a predetermined layer of the swollen absorbent material, the layer of the swollen absorbent material has a Ball Burst Strength (BBS) value of at least 30 gf in the BBS test.

In still another aspect of the invention, when the absorbent material swells by absorbing a urine and is formed into a predetermined layer of the swollen absorbent material, the layer of the swollen absorbent material has a Compression Recovery (CR) value of at least 15% in the CR test.

In yet another aspect of the invention, the plurality of absorbent gelling particles are spontaneously connective through the absorbent property modification polymer in response to an application of a urine.

The present invention further relates to absorbent articles. In still another aspect of the invention, an absorbent article comprises: (a) a liquid pervious topsheet; (b) a liquid impervious backsheet; and (c) an absorbent core positioned between the topsheet and the backsheet, wherein the absorbent core comprises at least one of the above described absorbent members.

DETAILED DESCRIPTION OF THE INVENTION

A. Definitions

Figure 1:
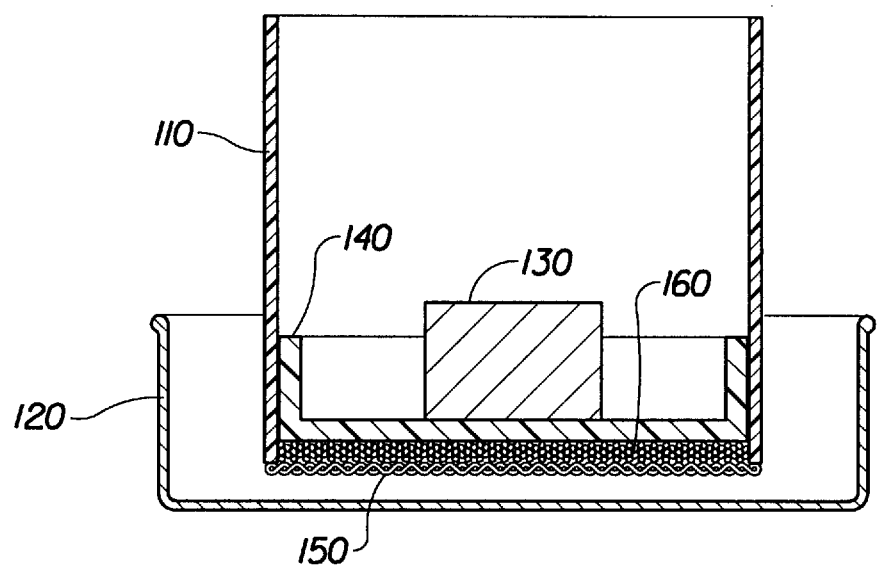
FIG. 1 is a schematic view of an apparatus for measuring the Gel Bulk Density (GBD) value of the absorbent materials.

As used herein, the term "body fluids" includes urine, blood, menses and vaginal discharges.

As used herein, the term "absorbent core" refers to the component of the absorbent article that is primarily responsible for fluid handling properties of the article, including acquiring, transporting, distributing and storing body fluids. As such, the absorbent core typically does not include the topsheet or backsheet of the absorbent article.

As used herein, the term "absorbent member" refers to the components of the absorbent core that typically provide one or more fluid handling properties, e.g., fluid acquisition, fluid distribution, fluid transportation, fluid storage, etc. The absorbent member can comprise the entire absorbent core or only a portion of the absorbent core, i.e., the absorbent core can comprise one or more absorbent members.

As used herein, the term "region" refers to portions or sections of the absorbent member.

As use herein, the term "layer" refers to an absorbent member whose primary dimension is X-Y, i.e., along its length and width, however, it should be noted that the layer has thickness.

B. Absorbent Members of the Invention

Absorbent members of the present invention are capable of absorbing large quantities of liquids such as water, body fluids, industrial fluids and household fluids and are capable of retaining such liquids under moderate pressure. In particular, absorbent materials included in the absorbent members of the present invention will swell generally isotropically and absorb rapidly the liquids.

Briefly stated, an absorbent member of the present invention comprises at least one region which comprises an absorbent material. The absorbent material comprises a mixture of (1) a plurality of absorbent gelling particles comprising a water-insoluble, water-swellable polymer, and (2) an absorbent property modification polymer reactive with at least one component included in a urine.

In the mixture, the absorbent property modification polymer is to be on at least a portion of the surface area of the absorbent gelling particles, preferably 70%, most preferably more than 90% of the all surface area of the absorbent gelling particles.

In a preferred embodiment, the absorbent material is in a concentration of at least 40%, more preferably from about 60 to 100% by weight in the region. In a more preferred embodiment, the absorbent member comprises fibrous matrix wherein the absorbent material is distributed in the fibrous matrix.

In preferred embodiments, there is less covalent bonds between the absorbent property modification polymer and the absorbent gelling particles. In a most preferred embodiment, there is no chemical bonds between the absorbent property modification polymer and the absorbent gelling particles. In such embodiments, most of the absorbent property modification polymer is only associated to the absorbent gelling particles via inter-molecular interactions such as electrostatic interaction, hydrogen bonding interaction, and van der Waals interactions. Therefore, the existence of the absorbent property modification polymer on the absorbent gelling particles gives little effect to the gel volume of the absorbent gelling particles. Preferably, the existence of the absorbent property modification polymer causes less than 10% change of the gel volume of the resultant absorbent material. This can be also achieved by less amount of chemical and/or physical bondings between the absorbent property modification polymer and the absorbent gelling particles.

If there are certain chemical bonds between the absorbent property modification polymer and the absorbent gelling particles, it is preferred that the type and extent of such chemical bonds have little effect on the gel volume of the resultant absorbent material. The decrease in gel volume due to the association of the absorbent property modification polymer with the absorbent gelling particles is preferred to be less than 10%. Preferably, almost all functional groups of the absorbent property modification polymer are not used for bonding the absorbent property modification polymer to the absorbent polymer of the absorbent material. These unused functional groups are preferably used for the bonds among the absorbent gelling particles after an application of a urine.

Consequently, the absorbent gelling particles can be spontaneously connective through the absorbent property modification polymer in response to an application of a urine. Consequently, when the absorbent material is provided in the region at a high concentration (e.g., more than 90%), the absorbent material is formed into a porous aggregate of the swollen particles after an application of a urine.

It should be noted that the unused functional groups of the absorbent property modification polymer of the absorbent material can be also reactive with the extractable components included in the hydrogel-forming absorbent polymers. More specifically, the absorbent property modification polymer is capable of trapping the extracted components which may cause a change of the characteristics of the body fluid. Therefore, the presence of the absorbent property modification polymer can lower the level of the extractable components of the absorbent material.

Absorbent materials used in the present invention have at least one improved absorbent property. The absorbent property can be improved by changing at least one physical property after swelling of the absorbent material. The "physical property" herein used includes (1) porosity, (2) liquid permeability, (3) wet integrity, and (4) recovery property when subjected to external forces, of an absorbent material after swelling by absorbing liquids.

The porosity of an absorbent material after swelling is evaluated by conducting the Gel Bulk Density (GBD) test. The liquid permeability of an absorbent material after swelling can be evaluated by conducting the Saline Flow Conductivity (SFC) test. The wet integrity of an absorbent material after swelling is evaluated by conducting the Ball Burst Strength (BBS) test. The recovery property of an absorbent material after swelling is evaluated by conducting the Compression Recovery (CR) test. The test methods for evaluating these properties as well as the gel volume and extractable components will be described in detail in the "Test Methods" section.

In one aspect of the present invention, the absorbent material used in the absorbent member has such an improved absorbent property that when the absorbent material swells by absorbing a urine and is formed into a predetermined layer of the swollen absorbent material under a predetermined load, the layer of the swollen absorbent material has a Gel Bulk Density (GBD) value of below 0.95 g/cm$^3$ in the GBD test.

GBD is an important physical property after swelling of the absorbent materials used in the present invention. This is to show their gel bulk density when swollen with body fluids so as to form a hydrogel zone or layer. This density is defined herein in terms of the GBD value of the absorbent material. GBD measures the weight per unit volume of a gel layer formed from the swollen absorbent material, including voids inherent in the gel layer. In other words, GBD is a measure of the porosity of swollen absorbent materials. It is anticipated that GBD value has a relationship with the SFC value described hereinafter.

The GBD value of the absorbent materials used in the present invention is below about 0.95 g/cm$^3$, preferably below about 0.9 g/cm$^3$, and most preferably below about 0.85 g/cm$^3$. Typically, these GBD values are in the range of from about 0.5 to about 0.9 g/cm$^3$, more typically from about 0.7 to about 0.85 g/cm$^3$.

In another aspect of the present invention, the absorbent material used in the absorbent member has such an improved property that when the absorbent material swells by absorbing a urine and is formed into a predetermined layer of the swollen absorbent material, the layer of the swollen absorbent material has a Saline Flow Conductivity (SFC) value of at least $20 \times 10^{-7}$ cm$^3$sec/g in the SFC test.

SFC is another important physical property after swelling of the absorbent materials used in the present invention. This is to show their liquid permeability or flow conductivity when swollen with body fluids so as to form a hydrogel zone or layer. SFC measures the ability of a swollen absorbent material to transport saline fluids therethrough. In other words, it shows the ability of a gel layer formed from the swollen absorbent material to transport liquids.

The SFC value of the absorbent materials after swelling of the present invention is at least about $20 \times 10^{-7}$ cm$^3$sec/g, preferably at least about $40 \times 10^{-7}$ cm$^3$sec/g, and most preferably at least about $100 \times 10^{-7}$ cm$^3$sec/g. Typically, these SFC values are in the range of from about 40 to about $300 \times 10^{-7}$ cm$^3$sec/g, more typically from about 60 to about $150 \times 10^{-7}$ cm$^3$sec/g.

It is believed that when an absorbent material is present at a high concentration in an absorbent member and then swells to form a hydrogel under usage pressures, the boundaries of the hydrogel come into contact, and interstitial voids in this high-concentration region become generally bounded by hydrogel When this occurs, it is believed the porosity and/or the permeability or flow conductivity properties of this region are generally reflective of the porosity and/or the permeability or flow conductivity properties of a hydrogel zone or layer formed from the swollen absorbent material alone. It is further believed that increasing the porosity and/or the permeability of these swollen high-concentration regions to levels that approach or even exceed conventional acquisition/distribution materials, such as wood-pulp fluff, can provide superior fluid handling properties for the absorbent member and absorbent core, thus decreasing incidents of leakage, especially at high fluid loadings. (Higher SFC values also are reflective of the ability of the formed hydrogel to acquire body fluids under normal usage conditions.)

In yet another aspect of the present invention, an absorbent material has such an improved absorbent property that when the absorbent material swells by absorbing a urine and is formed into a predetermined layer of the swollen absorbent material, the layer of the swollen absorbent material has a Ball Burst Strength (BBS) value of at least 30 gf in the BBS test.

BBS is another important physical property after swelling of the absorbent materials used in the present invention. This is to show their bursting peak load when swollen with body fluids so as to form a hydrogel zone or layer. BBS measures the force (or peak load) required to produce rupture of a gel layer formed from the swollen absorbent material.

BBS values of the absorbent materials after swelling of the present invention is at least about 30 gf in the BBS test, preferably at least about 50 gf, and most preferably at least about 100 gf. Typically, these BBS values are in the range of from about 50 to about 400 gf, more typically from about 100 to about 300 gf It is believed that when a conventional absorbent polymer is present at high concentrations in an absorbent member and then swells to form a hydrogel, the hydrogel is pushed by the usage pressures applied thereto and may move towards a edge portion of the absorbent member or core, and the absorbent article. When this occurs, a leakage of the hydrogel may be caused from the edge portion of the absorbent article, thus, a "gel-on-shin" problem is caused by using a conventional absorbent polymer. Since the absorbent materials of the present invention have improved wet integrity, in other words, bondings among the swollen absorbent particles of the absorbent material are more strength, and the individual swollen gel particles are not mobile, the leakage of swollen absorbent materials from absorbent articles can be prevented.

In still another aspect of the present invention, an absorbent material has such an improved absorbent property that when the absorbent material swells by absorbing a urine and is formed into a predetermined layer of the swollen absorbent material, the layer of the swollen absorbent material has a Compression Recovery (CR) value of at least 15% in the CR test.

CR is another important physical property after swelling of the absorbent materials used in the present invention. This is to show their compression recovery when swollen with body fluids so as to form a hydrogel zone or layer. CR measures the ability of the extent that an absorbent material at wet state has returned to its original shape/state when subjected to external forces.

CR values of the absorbent materials after swelling of the present invention is preferably at least about 20%, and most preferably at least about 30%. Typically, these CR values are in the range of from about 20 to about 80%, more typically from about 30 to about 70%.

It is believed that when a conventional absorbent polymer is present at a high concentration in an absorbent member and then swells to form a hydrogel, the hydrogel looks and feels jelly and mushy. In particular, when a user and/or consumer touches the absorbent article from the outside, the absorbent article gives such undesirable feeling to the user and/or consumer. Since the absorbent materials of the present invention have such improved CR values, the undesirable feeling (i.e., jelly/mushy feel) to the user and/or consumer can be prevented.

In a preferred embodiment, an absorbent material used in the present invention can be formed in a porous structure. As used herein, the terms "porous structure" mean a structure forming walls surrounding and defining cellular voids of absorbent polymers when substantially dry. In general a porous structure of absorbent material can provide the porous absorbent material with low density and/or high specific surface area. Under microscopic observations, walls formed in a porous absorbent material, for example, show the sponge-like appearance and/or the withered leaf-like appearance. Preferred examples of porous structures of absorbent materials and processes therefor disclosed in the co-pending U.S. application Ser. No. 197,913, entitled "Absorbent Materials Having Modified Surface Characteristics And Methods For Making The Same", Attorney Docket No. JA-80U, filed Feb. 17, 1994, incorporated herein by reference.

C. Absorbent Materials Used in the Invention

1. Absorbent Property Modification Polymers

Absorbent property modification polymers used in the present invention are reactive with at least one component included in a urine.

The term "reactive" used herein means that a substances (i.e. compound or ion) has an ability of interacting with another substances to cause changes in chemical and/or physical properties. Therefore, absorbent property modification polymers used in the present invention have an ability of interacting with at least one component included in a urine. In a preferred embodiment, the absorbent property modification polymer has an ability of interacting with a phosphate ion of urine through electrostatic interaction.

A practical method for determining whether an absorbent property modification polymer is reactive with at least one component included in a urine or not is mixing an aqueous solution of the absorbent property modification polymer with a urine. If the resultant mixture solution becomes cloudy, the absorbent property modification polymer can be determined as reactive with at least one component included in the urine.

The term "urine" used herein should be understood in general. A typical example of content of "normal urine" is disclosed in the book entitled "Textbook of Medical Physiology" by Arthur C. Guyton (W. B. Saunders Company, 1991, page 304), which is incorporated herein by reference. It should be noted that Jayco Synthetis Urine is used for all measurements described hereinafter. In general, a urine contains an anion having at least two ionic charge numbers, such as a phosphate ion, a sulfate ion, and carbonate ion.

In preferred an embodiment, the absorbent property modification polymer can render the absorbent gelling particles spontaneously connective through the absorbent property modification polymer in response to an application of a urine.

The term "connective" used herein means that a plurality of materials has an ability of connecting with each other.

Therefore, the absorbent gelling particles of the absorbent material can have an ability of connecting with each other after urine is applied to the absorbent material.

In a more preferred embodiment, the absorbent property modification polymer is a cationic polymer which can be reactive with at least one component included in a urine. Preferably, the cationic polymer is capable of having an electrostatic interaction with an acidic group such as a carboxyl group of absorbent polymer. Therefore, in a further preferred embodiment, the cationic polymer is capable of bonding to both the anion included in a urine and the absorbent polymer.

Preferred cationic polymers can include polyamine or polyimine materials which are reactive with at least one component included in a urine. The polyamine material preferably used in the present invention is selected from the group consisting of (1) polymers having primary amine groups (e.g., polyvinylamine, polyallyl amine); (2) polymers having secondary amine groups (e.g., polyethyleneimine); and (3) polymers having tertiary amine groups (e.g., poly N,N-dimethylalkyl amine).

Practical examples of the cationic polymer are, for example, polyethyleneimine, a modified polyethyleneimine which is crosslinked by epihalohydrine in a range soluble in water, polyamine, a modified polyamidoamine by graft of ethyleneimine, polyetheramine, polyvinylamine, polyalkylamine, polyamidopolyamine, and polyallylamine.

In preferred embodiments, a cationic polymer has at least 500 of the molecular weight in average, more preferably 5,000, most preferably 10,000 or more. Cationic polymers having 500 or more of the weight-average molecular weight used in the present invention are not limited to polymers showing a single maximum value (a peak) in a molecular weight analysis by gel permeation chromatography, and polymers having a weight-average molecular weight of 500 or more may be used even if it exhibits a plural maximum value (peaks).

A preferable amount of the cationic polymer is in a range of from about 0.05 to 20 parts by weight against 100 parts by weight of the absorbent polymer particle, more preferably from about 0.3 to 10 parts by weight, and most preferably from about 0.5 to 5 parts by weight.

2. Absorbent Gelling Particles (1) Chemical Composition

The water-insoluble, water-swellable absorbent polymers useful in the present invention are commonly referred to as "hydrogel-forming", "hydrocolloids", or "superabsorbent" polymers and can include polysaccharides such as carboxymethyl starch, carboxymethyl cellulose, and hydroxypropyl cellulose; nonionic types such as polyvinyl alcohol, and polyvinyl ethers; cationic types such as polyvinyl pyridine, polyvinyl morpholinione, and N,N-dimethylaminoethyl or N,N-diethylaminopropyl acrylates and methacrylates, and the respective quaternary salts thereof. Typically, hydrogel-forming absorbent polymers useful in the present invention have a multiplicity of anionic, functional groups, such as sulfonic acid, and more typically carboxy, groups. Examples of polymers suitable for use herein include those which are prepared from polymerizable, unsaturated, acid-containing monomers. Thus, such monomers include the olefinically unsaturated acids and anhydrides that contain at least one carbon to carbon olefinic double bond. More specifically, these monomers can be selected from olefinically unsaturated carboxylic acids and acid anhydrides, olefinically unsaturated sulfonic acids, and mixtures thereof.

Some non-acid monomers can also be included, usually in minor amounts, in preparing the hydrogel-forming absorbent polymers herein. Such non-acid monomers can include, for example, the water-soluble or water-dispersible esters of the acid-containing monomers, as well as monomers that contain no carboxylic or sulfonic acid groups at all. Optional non-acid monomers can thus include monomers containing the following types of functional groups: carboxylic acid or sulfonic acid esters, hydroxyl groups, amide-groups, amino groups, nitrile groups, quaternary ammonium salt groups, aryl groups (e.g., phenyl groups, such as those derived from styrene monomer). These non-acid monomers are well-known materials and are described in greater detail, for example, in U.S. Pat. No. 4,076,663 (Masuda et al), issued Feb. 28, 1978, and in U.S. Pat. No. 4,062,817 (Westerman), issued Dec. 13, 1977, both of which are incorporated by reference.

Olefinically unsaturated carboxylic acid and carboxylic acid anhydride monomers include the acrylic acids typified by acrylic acid itself, methacrylic acid, ethacrylic acid, -chloroacrylic acid, a-cyanoacrylic acid, -methylacrylic acid (crotonic acid), -phenylacrylic acid, -acryloxypropionic acid, sorbic acid, -chlorosorbic acid, angelic acid, cinnamic acid, p-chlorocinnamic acid, -sterylacrylic acid, itaconic acid, citroconic acid, mesaconic acid, glutaconic acid, aconitic acid, maleic acid, fumaric acid, tricarboxyethylene and maleic acid anhydride.

Olefinically unsaturated sulfonic acid monomers include aliphatic or aromatic vinyl sulfonic acids such as vinylsulfonic acid, allyl sulfonic acid, vinyl toluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-methacryloxypropyl sulfonic acid and 2-acrylamide-2-methylpropane sulfonic acid.

Preferred hydrogel-forming absorbent polymers for use in the present invention contain carboxy groups. These polymers include hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. No. 3,661,875, U.S. Pat. No. 4,076,663, U.S. Pat. No. 4,093,776, U.S. Pat. No. 4,666,983, and U.S. Pat. No. 4,734,478.

Most preferred polymer materials for use in making the hydrogel-forming absorbent polymers are slightly network crosslinked polymers of partially neutralized polyacrylic acids and starch derivatives thereof. Most preferably, the hydrogel-forming absorbent polymers comprise from about 50 to about 95%, preferably about 75%, neutralized, slightly network crosslinked, polyacrylic acid (i.e., poly (sodium acrylate/acrylic acid) ). Network crosslinking renders the polymer substantially water-insoluble and, in part, determines the absorptive capacity and extractable polymer content characteristics of the hydrogel-forming absorbent polymers. Processes for network crosslinking these polymers and typical network crosslinking agents are described in greater detail in U.S. Pat. No. 4,076,663.

Further, surface crosslinked hydrogel-forming absorbent polymers can be preferably used in the present invention. They have a higher level of crosslinking in the vicinity of the surface than in the interior. As used herein, "surface" describes the outer-facing boundaries of the particle, fiber, etc. For porous hydrogel-forming absorbent polymers (e.g., porous particles, etc.), exposed internal boundaries can also be included. By a higher level of crosslinking at the surface, it is meant that the level of functional crosslinks for the hydrogel-forming absorbent polymer in the vicinity of the surface is generally higher than the level of functional crosslinks for the polymer in the interior.

The gradation in crosslinking from surface to interior can vary, both in depth and profile. Thus, for example, the depth of surface crosslinking can be shallow, with a relatively sharp transition to a lower level of crosslinking. Alternatively, for example, the depth of surface crosslinking can be a significant fraction of the dimensions of the hydrogel-forming absorbent polymer, with a broader transition.

Depending on size, shape, porosity as well as functional considerations, the degree and gradient of surface crosslinking can vary within a given hydrogel-forming absorbent polymer. For particulate hydrogel-forming absorbent polymers, surface crosslinking can vary with particle size, porosity, etc. Depending on variations in surface:volume ratio within the hydrogel-forming absorbent polymer (e.g., between small and large particles), it is not unusual for the overall level of crosslinking to vary within the material (e.g., be greater for smaller particles).

Surface crosslinking is generally accomplished after the final boundaries of the hydrogel-forming absorbent polymer are essentially established (e.g., by grinding, extruding, foaming, etc.) However, it is also possible to effect surface crosslinking concurrent with the creation of final boundaries. Furthermore, some additional changes in boundaries can occur even after surface crosslinks are introduced.

A number of processes for introducing surface crosslinks are disclosed in the art. These include those where: (i) a di- or poly-functional reagent(s) (e.g., glycerol, 1,3-dioxolan-2-one, polyvalent metal ions, polyquaternary arines) capable of reacting with existing functional groups within the hydrogel-forming absorbent polymer is applied to the surface of the hydrogel-forming absorbent polymer; (ii) a di- or poly-functional reagent that is capable of reacting with other added reagents and possibly existing functional groups within the hydrogel-forming absorbent polymer such as to increase the level of crosslinking at the surface is applied to the surface (e.g., the addition of monomer plus crosslinker and the initiation of a second polymerization reaction); (iii) no additional polyfunctional reagents are added, but additional reaction(s) is induced amongst existing components within the hydrogel-forming absorbent polymer either during or after the primary polymerization process such as to generate a higher level of crosslinking at or near the surface (e.g., heating to induce the formation of anhydride and or esters crosslinks between existing polymer carboxylic acid and/or hydroxyl groups and suspension polymerization processes wherein the crosslinker is inherently present at higher levels near the surface); and (iv) other materials are added to the surface such as to induce a higher level of crosslinking or otherwise reduce the surface deformability of the resultant hydrogel. Combinations of these surface crosslinking processes either concurrently or in sequence can also be employed. In addition to crosslinking reagents, other components can be added to the surface to aid/control the distribution of crosslinking (e.g., the spreading and penetration of the surface crosslinking reagents.)

Suitable general methods for carrying out surface crosslinking of hydrogel-forming absorbent polymers according to the present invention are disclosed in U.S. Pat. No. 4,541,871 (Obayashi), issued Sep. 17, 1985; published PCT application WO92/16565 (Stanley), published Oct. 1, 1992, published PCT application WO90/08789 (Tai), published Aug. 9, 1990; published PCT application WO93/05080 (Stanley), published Mar. 18, 1993; U.S. Pat. No. 4,824,901 (Alexander), issued Apr. 25, 1989; U.S. Pat. No. 4,789,861 (Johnson), issued Jan. 17, 1989; U.S. Pat. No. 4,587,308 (Makita), issued May 6, 1986; U.S. Pat. No. 4,734,478 (Tsubakimoto), issued Mar. 29, 1988; U.S. Pat. No. 5,164,459 (Kimura et. al.), issued Nov. 17, 1992; published German patent application 4,020,780 (Dahmen), published Aug. 29, 1991; and published European patent application 509,708 (Gartner), published Oct. 21, 1992; all of which are incorporated by reference.

While the hydrogel-forming absorbent polymer is preferably of one type (i.e., homogeneous), mixtures of polymers can also be used in the present invention. For example, mixtures of starch-acrylic acid graft copolymers and slightly network crosslinked polymers of partially neutralized polyacrylic acid can be used in the present invention.

(2) Physical Forms

The absorbent gelling particles used in the present invention can have a size, shape and/or morphology varying over a wide range. The absorbent gelling particles do not have a large ratio of greatest dimension to smallest dimension (e.g., granules, flakes, pulverulents, interparticle aggregates, interparticle crosslinked aggregates, and the like) and can be in the form of fibers, foams, and the like. The hydrogel-forming absorbent polymers can also comprise mixtures with low levels of one or more additives, such as for example powdered silica, surfactants, glue, binders, and the like. The components in this mixture can be physically and/or chemically associated in a form such that the hydrogel-forming polymer component and the non-hydrogel-forming polymer additive are not readily physically separable.

The hydrogel-forming absorbent polymers can be essentially non-porous or have substantial internal porosity.

For particles as described above, particle size is defined as the dimension determined by sieve size analysis. Thus, for example, a particle that is retained on a U.S.A. Standard Testing Sieve with 710 micron openings (e.g., No. 25 U.S. Series Alternate Sieve Designation) is considered to have a size greater than 710 microns; a particle that passes through a sieve with 710 micron openings and is retained on a sieve with 500 micron openings (e.g., No. 35 U.S., Series Alternate Sieve Designation) is considered to have a particle size between 500 and 710 microns; and a particle that passes through a sieve with 500 micron openings is considered to have a size less than 500 microns. The mass median particle size of a given sample of hydrogel-forming absorbent polymer particles is defined as the particle size that divides the sample in half on a mass basis, i.e., one-half of the sample by weight will have a particle size less than the mass median size and one-half of the sample will have a particle size greater than the mass median size. A standard particle-size plotting method (wherein the cumulative weight percent of the particle sample retained on or passed through a given sieve size opening is plotted versus sieve size opening on probability paper) is typically used to determine mass median particle size when the 50% mass value does not correspond to the size opening of a U.S.A. Standard Testing Sieve. These methods for determining particle sizes of the hydrogel-forming absorbent polymer particles are further described in U.S. Pat. No. 5,061,259 (Goldman et. al), issued Oct. 29, 1991, which is incorporated by reference.

For particles of hydrogel-forming absorbent polymers useful in the present invention, the particles will generally range in size from about 1 to about 2000 microns, more preferably from about 20 to about 1000 microns. The mass median particle size will generally be from about 20 to about 1500 microns, more preferably from about 50 microns to about 1000 microns, and even more preferably from about 100 to about 800 microns.

Within these size ranges, it can be preferable to choose either larger or smaller particles depending on the need for faster or slower absorption kinetics. For example, for non-porous particles, the swelling rate will generally decrease with increasing particle size. It can also be preferable to choose either larger or smaller particles or narrower size cuts (fractions) of larger or smaller particles from the bulk polymer in order to increase the gel layer permeability (i.e., increase the Saline Flow Conductivity (SFC) value). For particles of some hydrogel-forming absorbent, polymers, it has been found that narrower size range cuts containing generally larger particle sizes within the above specified size ranges have higher SFC values without any significant degradation in other hydrogel-forming absorbent polymer properties such as Performance Under Pressure (PUP) capacity and level of extractable polymer. Thus, for example, it can be useful to use a size cut having a mass median size in the range of from about 500 to about 710 microns wherein only minimal mass fractions of the particulates have sizes either greater than about 710 microns or less than about 500 microns. Alternatively, a broader size cut wherein the particles generally have a size in the range of from about 150 microns to about 800 microns can be useful.

D. Process for Making Absorbent Materials

Briefly stated, absorbent materials used in the present invention can be made by mixing an absorbent property modification polymer reactive with at least one component included in a urine with a plurality of absorbent gelling particles comprising a water-insoluble, water-swellable absorbent polymer. More specifically, the mixture can be made by applying the absorbent property modification polymer onto the absorbent gelling particles. As used herein, the term "apply onto" means that the absorbent property modification polymer will be on at least a portion of the surface area of the absorbent gelling particles. Preferably, the absorbent property modification polymer is applied onto all of the surface of the absorbent gelling particles.

In a case where the absorbent property modification polymer is in the form of a small particle or powder, the absorbent property modification polymer can be applied by any of various techniques and apparatus used for applying a material to another material. In another case where the absorbent property modification polymer is in the form of a liquid, the absorbent property modification polymer can be applied by any of various techniques and apparatus used for applying a liquid to a material. As a result, absorbent materials of the present invention can be obtained in the forms of the above described mixtures.

In a preferred embodiment, an absorbent property modification polymer (e.g., a cationic polymer or a polyamine or polyimine material) which is reactive with at least one component included in a urine is dissolved into a solvent to make a solution. The absorbent property modification polymer can be dissolved in the solvent by any of various techniques and apparatus used for dissolving a material to a solvent known in the art. In more preferred embodiments, an organic solvent is used as the solvent. Preferably, the concentration of the absorbent property modification polymer in the solution by weight is from about 0.05% to 60%, more preferably, from 0.5% to 30%.

In preferred embodiments, an absorbent property modification polymer which is insoluble in an organic solvent can be used. In more preferred embodiments, a polar organic solvent is used as the solvent. In such embodiments, a mixture solvent of a hydrophilic organic solvent and water is used as the solvent for the absorbent property modification polymer. Non-limiting examples of the preferred organic solvent includes: the low molecular weight alcohols such as methanol, ethanol, or propanol; acetone; dimethylformamide(DMF); dimethylsulfoxide(DMSO); hexylmethylphosphoric triamide(HMPT); and mixtures thereof. In alternative preferred embodiments, non-polar solvents such as hexane, toluene, xylene, and benzene can be used as one of the organic solvent.

Preferably, the weight ratio of the organic solvent to water is about at least 50:50, more preferably from about 70:30 to about 98:2.

After preparing the solution, the solution is applied onto the absorbent gelling particles thereby making a intermittent mixture. More specifically, an amount of the solution is applied onto the absorbent gelling particles. The solution can be applied by any of various techniques and apparatus used for applying a solution to a material including coating, dumping, pouring, dropping, spraying, atomizing, condensing, or immersing the liquid mixture onto the absorbent gelling particles. Thus, in the intermittent mixture the solution will be on at least a portion of the surface area of the absorbent gelling particles. Preferably, the solution will be on all of the surface of the absorbent gelling particles.

The amount of the absorbent property modification polymer which is sufficient to effect an enhancement of the physical properties of the absorbent material can vary on a number of factors such as the chemical composition of the absorbent polymer and the physical forms of the absorbent gelling particles, e.g., particle size of the absorbent particles, and the chemical composition and molecular weight of the absorbent property modification polymer, as well as on the applying method thereof.

In preferred embodiments, the weight ratio of the absorbent property modification polymer to the absorbent gelling particles is from about 0.05:100 to about 20:100, more preferably from about 0.5:100 to about 5:100.

After making the intermittent mixture, at least a portion of the solvent is removed from the intermittent mixture. Preferably, at least about 80%, more preferably more than 95%, most preferably about 100% of the solvent is removed from the intermittent mixture. The removal of the solvent can be made by any of various techniques and apparatus used for separating or removing liquids from liquid-solid mixtures, including evaporation, filtration, washing, or a combination thereof.

In a preferred embodiment, the physical property modification polymer is applied onto the absorbent gelling particles after the treatment of the surface crosslinking of the absorbent gelling particles. On the other hand, in another embodiment the physical property modification polymer is applied onto the absorbent gelling particles before the treatment of the surface crosslinking of the absorbent gelling particles. In addition, in a further embodiment the application of the physical property modification polymer and the treatment of the cross linking can be carried out at the same time. It should be noted that in some embodiments the physical property modification polymer can be used as a cross linking agent.

In preferred embodiments, the resultant absorbent materials can have a number of shapes and sizes. For example, the absorbent materials can be typically in the form of particles, sheets, films, cylinders, blocks, fibers, filaments, or other shaped elements. More preferably, the absorbent material is particulate.

E. Absorbent Articles Using The Absorbent Members

The absorbent members according to the present invention can be used for many purposes in many fields of use. For example, the absorbent members can be used for packing containers; drug delivery devices; wound cleaning devices; burn treatment devices; ion exchange column materials; construction materials; agricultural or horticultural materials such as seed sheets or water-retentive materials; and industrial uses such as sludge or oil dewatering agents, materials for the prevention of dew formation, desiccants, and humidity control materials.

Because of the unique absorbent properties of the absorbent materials used in the present invention, they are especially suitable for use as absorbent cores in absorbent articles, especially disposable absorbent articles. As used herein, the term "absorbent article" refers to articles which absorb and contain body fluids and more specifically refers to articles which are placed against or in proximity to the body of the wearer to absorb and contain the various fluids discharged from the body. Additionally, "disposable" absorbent articles are those which are intended to be discarded after a single use (i.e., the original absorbent article in its whole is not intended to be laundered or otherwise restored or reused as an absorbent article, although certain materials or all of the absorbent article can be recycled, reused, or composted).

In general, an absorbent article comprises: (a) a liquid pervious topsheet which is located adjacent to the wearer's body; (b) a liquid impervious backsheet which is located distant from the wearer's body and adjacent to the wearer's clothing; and (c) an absorbent core positioned between the topsheet and the backsheet. The absorbent core comprises at least one of the above described absorbent members. In a preferred embodiment, the absorbent core is one of the above described absorbent members. Preferably, the absorbent core further comprises a substrate web wherein the absorbent material is attached to the substrate web. Alternatively, the absorbent core further comprises an envelope web encasing the absorbent material. In a further alternative embodiment, the absorbent core further comprises two layered tissues wherein the absorbent material is distributed between the two layered tissues.

In more preferred embodiments, the absorbent material in the absorbent core has a basis weight of from about 60 g/m$^2$ to about 1500 g/m$^2$, more preferably from about 100 g/m$^2$ to about 1000 g/m$^2$, most preferably from about 150 g/m$^2$ to about 500 g/m$^2$ of the absorbent material.

In some preferred embodiments, the absorbent core or absorbent member can further comprise fibers or fluff pulp (fibrous or fiber material), more specifically, non-absorbent-gelling fibers. Such fiber material can be used as reinforcing members in the absorbent core, improving fluid handling of the core, as well as a co-absorbent with the absorbent polymers. Preferably, the absorbent core or member includes from about 40% to about 100% by weight of the absorbent material and from about 60% to about 0% by weight of such non-absorbent-gelling fiber material distributed within the absorbent material.

Any type of fiber material which is suitable for use in conventional absorbent products can be used in the absorbent core or absorbent member herein. Specific examples of such fiber material include cellulose fibers, improved cellulose fibers, rayon, polypropylene, and polyester fibers such as polyethylene terephthalate (DACRON), hydrophilic nylon (HYDROFIL), and the like. Examples of other fiber materials for use in the present invention in addition to some already discussed are hydrophilized hydrophobic fibers, such as surfactant-treated or silica-treated thermoplastic fibers derived, for example, from polyolefins such as polyethylene or polypropylene, polyacrylics, polyamides, polystyrenes, polyurethanes and the like. In fact, hydrophilized hydrophobic fibers which are in and of themselves not very absorbent and which, therefore, do not provide webs of sufficient absorbent capacity to be useful in conventional absorbent structures, are suitable for use in the absorbent core by virtue of their good wicking properties. This is because, in the absorbent core herein, the wicking propensity of the fibers is as important, if not more important, than the absorbent capacity of the fiber material itself due to the high rate of fluid uptake and lack of gel blocking properties of the absorbent core. Synthetic fibers are generally preferred for use herein as the fiber component of the absorbent core. Most preferred are polyolefin fibers, preferably polyethylene fibers.

Other cellulosic fiber materials which can be useful in certain absorbent cores or absorbent members herein are chemically stiffened cellulosic fibers. Preferred chemically stiffened cellulosic fibers are the stiffened, twisted, curled cellulosic fibers which can be produced by internally crosslinking cellulose fibers with a crosslinking agent. Suitable stiffened, twisted, curled cellulose fibers useful as the hydrophilic fiber material herein are described in greater detail in U.S. Pat. No. 4,888,093 (Dean et al), issued Dec. 19, 1989; U.S. Pat. No. 4,889,595 (Herron et al), issued Dec. 26, 1989; U.S. Pat. No. 4,889,596 (Schoggen et al), issued Dec. 26, 1989; U.S. Pat. No. 4,889,597 (Bourbon et al), issued Dec. 26, 1989; and U.S. Pat. No. 4,898,647 (Moore et al), issued Feb. 6, 1990, all of which are incorporated by reference.

A preferred embodiment of the disposable absorbent article is a diaper. As used herein, the term "diaper" refers to a garment generally worn by infants and incontinent persons that is worn about the lower torso of the wearer. A preferred diaper configuration for a diaper comprising an absorbent core is described generally in U.S. Pat. No. 3,860,003 (Buell), issued Jan. 14, 1975, which is incorporated by reference. Alternatively preferred configurations for disposable diapers herein are also disclosed in U.S. Pat. No. 4,808,178 (Aziz et al), issued Feb. 28, 1989; U.S. Pat. No. 4,695,278 (Lawson), issued Sep. 22, 1987; U.S. Pat. No. 4,816,025 (Foreman), issued Mar. 28, 1989; and U.S. Pat. No. 5,151,092 (Buell et al.), issued Sep. 29, 1992, all of which are incorporated by reference.

Another preferred embodiment of the disposable absorbent article is a catamenial product. Preferred catamenial products comprise a formed-film, apertured topsheet as disclosed in U.S. Pat. No. 4,285,343 (McNair), issued Aug. 25, 1981; U.S. Pat. No. 4,608,047 (Mattingly), issued Aug. 26, 1986; and U.S. Pat. No. 4,687,478 (Van Tilburg), issued Aug. 18, 1987, all of which are incorporated by reference.

Preferred catamenial products can comprise wings, side flaps, and other structures and elements, as described in co-pending, commonly-assigned U.S. application Ser. No. 984,071, to Yasuko Morita, entitled "Absorbent Article Having Elasticized Side Flaps", Attorney Docket No. JA-09RM, filed Nov. 30, 1992, incorporated herein by reference.

It should be understood, however, that the present invention is also applicable to other absorbent articles known commercially by other names, such as incontinent briefs, adult incontinent products, training pants, diaper inserts, facial tissues, paper towels, and the like.

F. Test Methods

Synthetic Urine

The specific synthetic urine used in the test methods of the present invention is referred to herein as "Synthetic Urine". The Synthetic Urine is commonly known as Jayco SynUrine or Jayco Synthetis Urine and is available from Jayco Pharmaceuticals Company of Camp Hill, Pa. The formula for the Synthetic Urine is: 2.0 g/l of KCl; 2.0 g/l of $Na_2SO_4$; 0.85 g/l of $(NH_4)H_2PO_4$; 0.15 g/l $(NH_4)_2HPO_4$; 0.19 g/l of $CaCl_2$ and 0.23 g/l of $MgCl_2$. All of the chemicals are of reagent grade. The pH of the Synthetic Urine is in the range of 6.0 to 6.4.

1. Gel Bulk Density (GBD) Test

This test determines the gel bulk density (GBD) of an absorbent material that is swollen in Jayco synthetic urine. The GBD is the weight per unit volume of a swollen absorbent material, including voids inherent in the swollen gel material as tested.

The objective of this test is to assess the porosity of an absorbent material at wet state. GBD of an absorbent material is used as a measure of the gel porosity of an absorbent material after swelling in Jayco synthetic urine. Gel porosity here means the voids fraction in the swollen absorbent material or the fraction volume of the bulk gel layer that is not occupied by gel. An absorbent material that has lower GBD is likely to have more voids, in other words, to have higher porosity at wet state.

(1) Apparatus

A suitable GBD measurement apparatus is shown in FIG. 1. This apparatus comprises a cylinder 110, a cup-like pistol 140, a weight 130 that fits inside the pistol 140, and a flat-bottomed TEFLON tray 120. The cylinder 110 is bored from a transparent LEXAN rod (or equivalent, for example Acrylic rod) and has an inner diameter of 6.00 cm (area= 28.27 $cm^2$), with a wall thickness of approximately 0.5 cm, and a height of approximately 5.0 cm. The bottom of the cylinder is faced with a No. 400 mesh stainless-steel screen 150 that is biaxially stretched to tautness prior to attachment. The piston 140 is in the form of a TEFLON cup and is machined to fit into the cylinder 110 within tight tolerances. Stainless weight 130 is machined to fit within the pistol 140. The combined weight of piston 140 and weight 130 is 199 g, which corresponds to a pressure of 0.1 psi for an area of 28.27 $cm^2$.

The thickness of the gel layer 160 in cylinder 110 is measured to an accuracy of about 0.05 mm. Any method having the requisite accuracy can be used, as long as the weights are not removed and the gel layer is not additionally disturbed during the thickness measurement. Using a caliper gauge (e.g., Digimatic Caliper, Mitutoya Corp., Kyoto, or equivalent) to measure the gap between the top of the TEFLON pistol 140 and the top of the cylinder 110, relative to this gap with no absorbent material in the cylinder is acceptable.

The GBD measurement is performed at room temperature. Jayco synthetic urine is used in this test.

(2) Procedure 0.9 g aliquot of absorbent material is added to the cylinder 110 and dispersed evenly on the screen 150. For most absorbent materials, moisture content is typically less than 5%. For these, the quantity of absorbent material to be added can be determined on a wet-weight (as is) basis. For absorbent material having a moisture content greater than about 5%, the added absorbent material weight should be corrected for moisture (i.e., the added absorbent should be 0.9 gm on a dry-weight basis). Care is taken to prevent the absorbent material from adhering to the cylinder walls. Pistol 140 is inserted into cylinder 110 and positioned on top of the absorbent material 160. Weight 130 is then positioned in pistol 140.

The piston/cylinder apparatus with the absorbent material is then transferred to a flat-bottomed TEFLON tray 120. 18 Milliliters of Jayco synthetic urine is added to the tray 120. Time is recorded as soon as Jayco urine is poured in to the tray 120. Jayco synthetic urine from the tray passed through the stainless screen 150 and is absorbed by the absorbent material 160. As the absorbent material absorbs fluid, a gel layer is formed in the cylinder 110. Alter a time period of 30 minutes, the thickness of the gel layer is determined. Consequently, the predetermined layer of the swollen absorbent material for the GBD measurement has been prepared. The gap between the top of the TEFLON pistol 140 and the top of the cylinder 110 is measured (Ls). Relative to this gap with no absorbent material in the cylinder (Lc) is also measured. This difference between Lc and Ls is the thickness of the absorbent material gel layer ($L_g$). The piston/cylinder apparatus with swollen gel is weighted (Ws).

The GBD is calculated according to the equation:

$$GBD = (Ws - Wc)/(28.27 \times Lg)$$

Where GBD is the gel bulk density value (g/cm$^3$), Ws is the total weight of the piston/cylinder apparatus with swollen gel (g), Wc is the weight of pistol/cylinder without absorbent material (g), and Lg is the thickness of the swollen gel layer (cm).

2. Saline Flow Conductivity (SFC) Test

This test determines the Saline Flow Conductivity (SFC) of the gel layer formed from hydrogel-forming absorbent polymer that is swollen in Jayco synthetic urine under a confining pressure. The objective of this test is to assess the ability of the hydrogel layer formed from a hydrogel-forming absorbent polymer to acquire and distribute body fluids when the polymer is present at high concentrations in an absorbent member and exposed to usage mechanical pressures. Darcy's law and steady-state flow methods are used for determining saline flow conductivity. (See, for example, "Absorbency," ed. by P. K. Chattedjee, Elsevier, 1985, Pages 42–43 and "Chemical Engineering Vol. II, Third Edition, J. M. Coulson and J. F. Richardson, Pergamon Press, 1978, Pages 125–127.)

A predetermined layer of swollen absorbent material used for SFC measurements is formed by swelling an absorbent material in Jayco synthetic urine for a time period of 60 minutes. The hydrogel layer is formed and its flow conductivity measured under a mechanical confining pressure of 0.3 psi (about 2 kPa). Flow conductivity is measured using a 0.118 M NaCl solution. For a hydrogel-forming absorbent polymer whose uptake of Jayco synthetic urine versus time has substantially leveled off, this concentration of NaCl has been found to maintain the thickness of the hydrogel layer substantially constant during the measurement. For some hydrogel-forming absorbent polymers, small changes in hydrogel-layer thickness can occur as a result of polymer swelling, polymer deswelling, and/or changes in hydrogel-layer porosity. A constant hydrostatic pressure of 4920 dyne/cm$^2$ (5 cm of 0.118M NaCl) is used for the measurement.

Flow rate is determined by measuring the quantity of solution flowing through the hydrogel layer as a function of time. Flow rate can vary over the duration of the measurement. Reasons for flow-rate variation include changes in the thickness of the hydrogel layer and changes in the viscosity of interstitial fluid, as the fluid initially present in interstitial voids (which, for example, can contain dissolved extractable polymer) is replaced with NaCl solution. If flow rate is time dependent, then the initial flow rate, typically obtained by extrapolating the measured flow rates to zero time, is used to calculate flow conductivity. The saline flow conductivity is calculated from the initial flow rate, dimensions of the hydrogel layer, and hydrostatic pressure.

Figure 2:
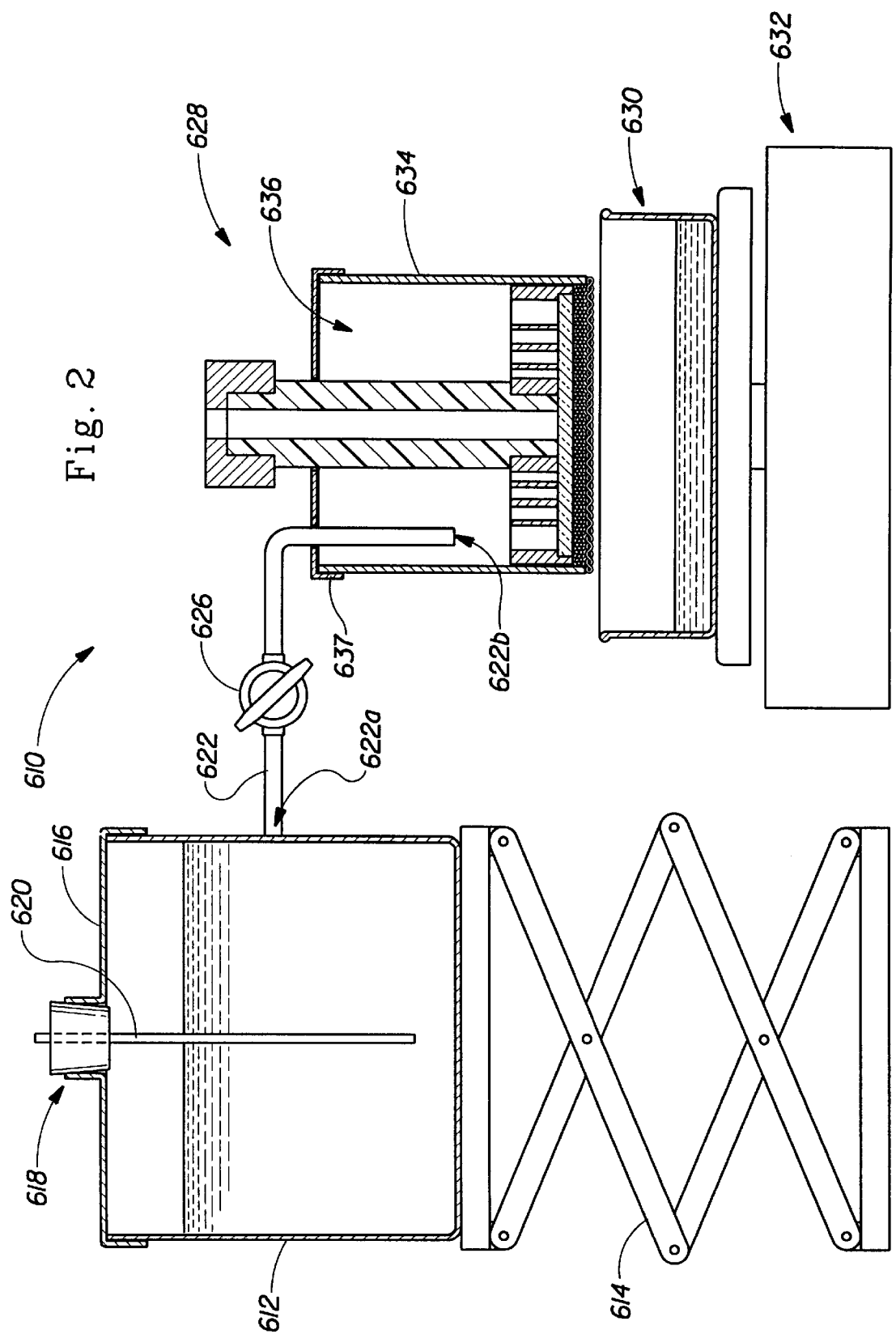
FIG. 2 is a schematic view of an apparatus for measuring the Saline Flow Conductivity (SFC) value of the absorbent materials.

A suitable apparatus 610 for this test is shown in FIG. 2. This apparatus includes a constant hydrostatic head reservoir indicated generally as 612 that sits on a laboratory jack indicated generally as 614. Reservoir 612 has lid 616 with a stoppered vent indicated by 618 so that additional fluid can be added to reservoir 612. An open-ended tube 620 is inserted through lid 616 to allow air to enter reservoir 612 for the purpose of delivering fluid at a constant hydrostatic pressure. The bottom end of tube 620 is positioned so as to maintain fluid in cylinder 634 at a height of 5.0 cm above the bottom of hydrogel layer 668 (see FIG. 3).

Reservoir 612 is provided with a generally L-shaped delivery tube 622 having an inlet 622a that is below the surface of the fluid in the reservoir. The delivery of fluid by tube 622 is controlled by stopcock 626. Tube 622 delivers fluid from reservoir 612 to a piston/cylinder assembly generally indicated as 628. Beneath assembly 628 is a support screen (not shown) and a collection reservoir 630 that sits on a laboratory balance 632.

Figure 3:
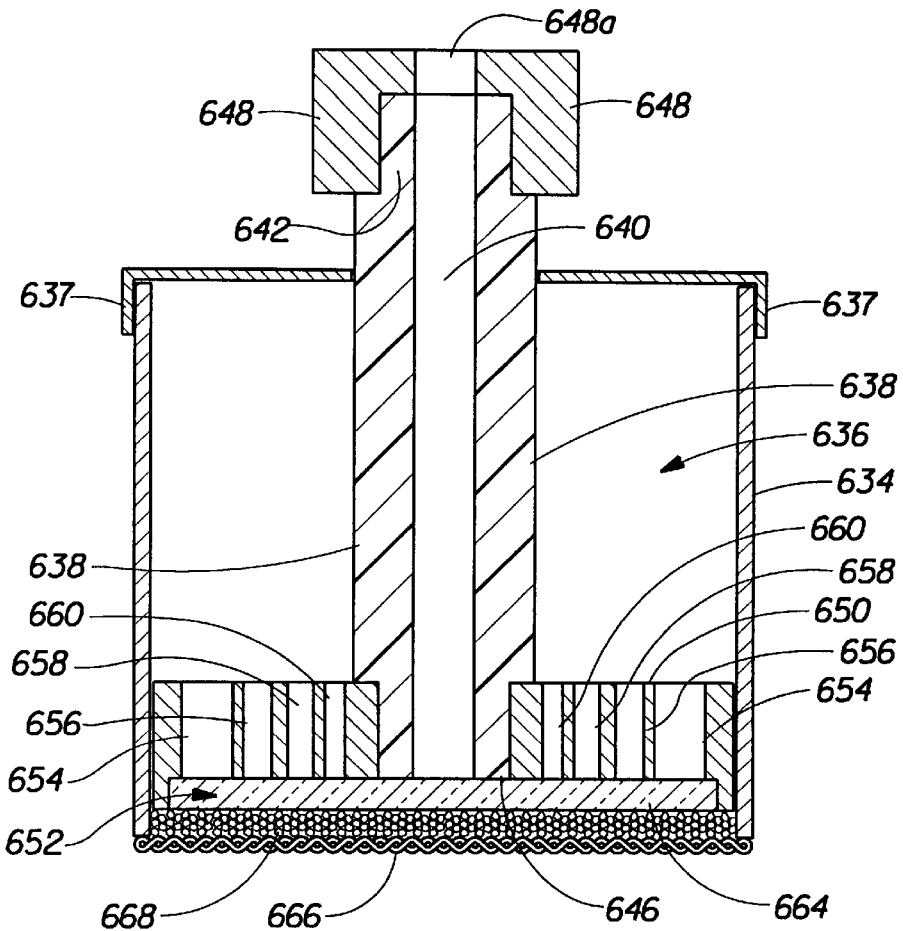
FIG. 3 represents an enlarged sectional view of the piston/cylinder assembly shown in FIG. 2.
Figure 7:
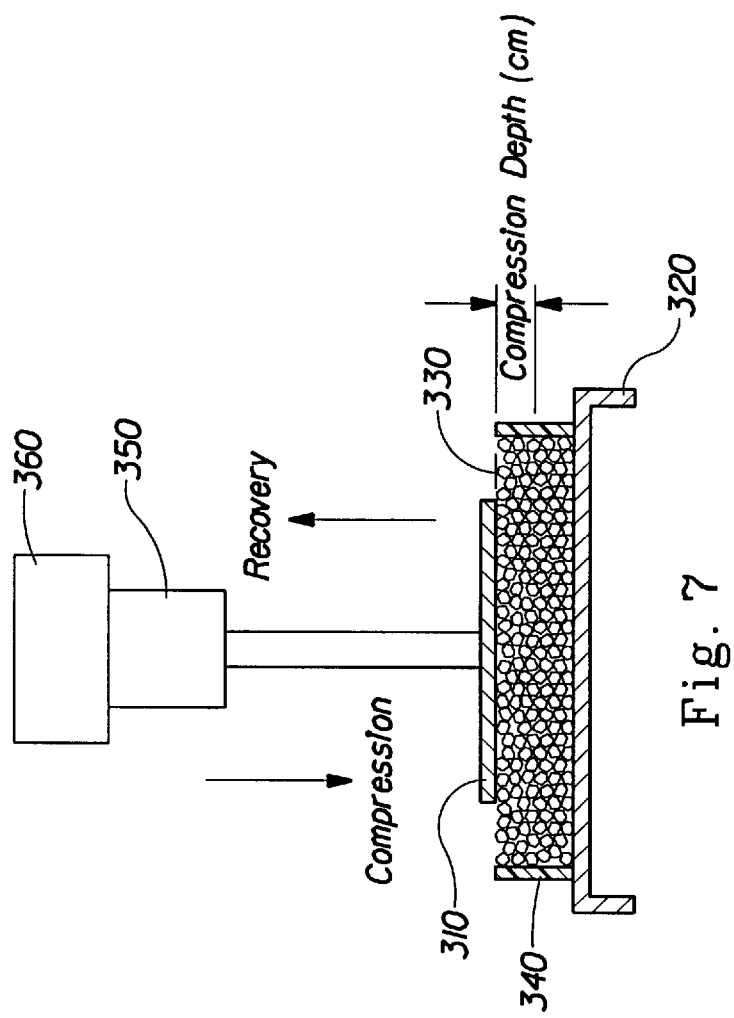
FIG. 7 is a schematic view of an apparatus for measuring the Compression Recovery (CR) value of the absorbent materials.

Referring to FIG. 2, assembly 628 basically consists of a cylinder 634, a piston generally indicated as 636 and a cover 637 provided with holes for piston 636 and delivery tube 622. As shown in FIG. 7, the outlet 622b of tube 622 is positioned below the bottom end of tube 620 and thus will also be below the surface of the fluid (not shown) in cylinder 634. As shown in FIG. 3, piston 636 consists of a generally cylindrical LEXAN® shaft 638 having a concentric cylindrical hole 640 bored down the longitudinal axis of the shaft. Both ends of shaft 638 are machined to provide ends 642 and 646. A weight indicated as 648 rests on end 642 and has a cylindrical hole 648a bored through the center thereof.

Figure 4:
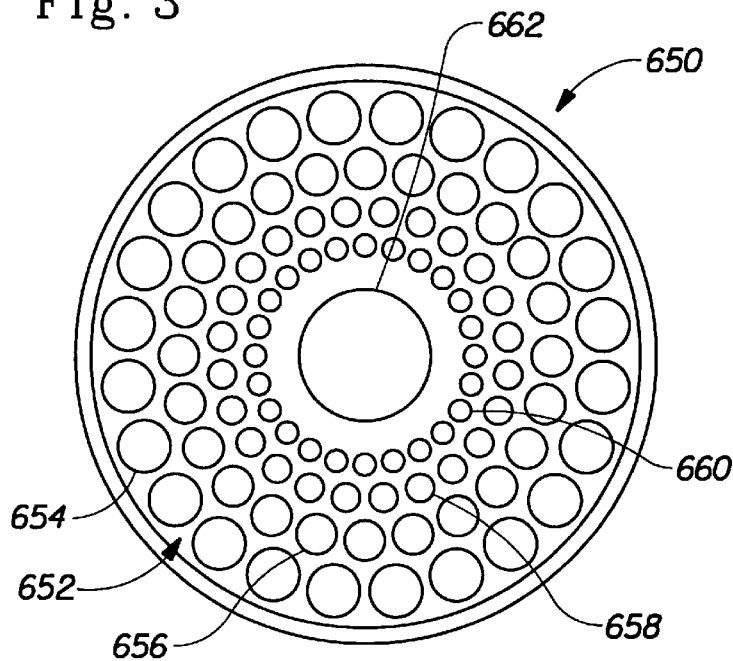
FIG. 4 represents a plan view of the bottom of the piston head from the piston/cylinder assembly shown in FIG. 3.

Inserted on the other end 646 is a generally circular Teflon piston head 650 having an annular recess 652 in the bottom thereof Piston head 650 is sized so as to slidably move inside cylinder 634. As particularly shown in FIG. 4, piston head 650 is provided with four concentric rings of twenty-four cylindrical holes each indicated generally as 654, 656, 658, and 660. As can be seen in FIG. 4, concentric rings 654 to 660 fit within the area defined by recess 652. The holes in each of these concentric rings are bored from the top to bottom of piston head 650. The holes in each ring are spaced by approximately 15 degrees and offset by approximately 7.5 degrees from the holes in adjacent rings. The holes in each ring have a progressively smaller diameter going inwardly from ring 654 (0.204 inch diameter) to ring 660 (0.111 inch diameter). Piston head 650 also has cylindrical hole 662 bored in the center thereof to receive end 646 of shaft 638.

As shown in FIG. 3, a fritted circular glass disc 664 fits within recess 652. Attached to bottom end of cylinder 634 is a No. 400 mesh stainless steel cloth screen 666 that is biaxially stretched to tautness prior to attachment. The sample of hydrogel-forming absorbent polymer indicated as 668 is supported on screen 666.

Cylinder 634 is bored from a transparent LEXAN® rod or equivalent and has an inner diameter of 6.00 cm (area=28.27 cm$^2$), a wall thickness of approximately 0.5 cm, and a height of approximately 6.0 cm. Piston head 650 is machined from a solid Teflon rod. It has a height of 0.625 inches and a diameter that is slightly less than the inner diameter of cylinder 634, so that it fits within the cylinder with minimum wall clearances, but still slides freely. Recess 652 is approximately 56 mm in diameter by 4 mm deep. Hole 662 in the center of the piston head 650 has a threaded 0.625 inch opening (18 threads/inch) for end 646 of shaft 638. Fritted disc 664 is chosen for high permeability (e.g., Chemglass Cat No. CG-201-40, 60 mm diameter; X-Coarse Porosity) and is ground so that it fits snugly within recess 652 of piston head 650, with the bottom of the disc being flush with the bottom of the piston head. Shaft 638 is machined from a LEXAN® rod and has an outer diameter of 0.875 inches and an inner diameter of 0.250 inches. End 646 is approximately 0.5 inches long and is threaded to match hole 662 in piston head 650. End 642 is approximately an inch long and 0.623 inches in diameter, forming an annular shoulder to support the stainless steel weight 648. Fluid passing through the hole 640 in shaft 638 can directly access the flitted disc 664. The annular stainless steel weight 648 has an inner diameter of 0.625 inches, so that it slips onto end 642 of shaft 638 and rests on the annular shoulder formed therein. The combined weight of fritted glass disc 664, piston 636 and weight 648 equals 596 g, which corresponds to a pressure of 0.3 psi for an area of 28.27 $cm^2$. Cover 637 is machined from LEXAN® or its equivalent and is dimensioned to cover the top of cylinder 634. It has an 0.877 inch opening in the center thereof for shaft 638 of piston 636 and a second opening near the edge thereof for delivery tube 622.

The cylinder 634 rests on a 16 mesh rigid stainless steel support screen (not shown) or equivalent. This support screen is sufficiently permeable so as to not impede fluid flow into the collection reservoir 630. The support screen is generally used to support cylinder 634 when the flow rate of saline solution through assembly 628 is greater than about 0.02 g/sec. For flow rates less than about 0.02 g/sec, it is preferable that there be a continuous fluid path between cylinder 634 and the collection reservoir.

The 0.118M NaCl solution is prepared by dissolving 6.896 g NaCl (Baker Analyzed Reagent or equivalent) to 1.0 liters with distilled water.

An analytical balance 632 accurate to 0.01 g (e.g., Mettler PM4000 or equivalent) is typically used to measure the quantity of fluid flowing through the hydrogel layer 668 when the flow rate is about 0.02 g/sec or greater. The balance is preferably interfaced to a computer for monitoring fluid quantity versus time.

The thickness of hydrogel layer 668 in cylinder 634 is measured to an accuracy of about 0.1 mm. Any method having the requisite accuracy can be used, as long as the weights are not removed and the hydrogel layer is not additionally compressed or disturbed during the measurement. Using a caliper gauge (e.g., Manostat 15-100-500 or equivalent) to measure the vertical distance between the bottom of the stainless steel weight 648 and the top of cover 637, relative to this distance with no hydrogel layer 668 in cylinder 634 is acceptable.

The SFC measurement is performed at ambient temperature (i.e., 20°–25° C.) and is carried out as follows:

0.9 g aliquot of hydrogel-forming absorbent polymer (corresponding to a basis weight of 0.032 $g/cm^2$) is added to cylinder 634 and distributed evenly on screen 666. For most hydrogel-forming absorbent polymers, moisture content is typically less than 5%. For these, the quantity of hydrogel-forming absorbent polymer to be added can be determined on a wet-weight (as is) basis. For hydrogel-forming absorbent polymers having a moisture content greater than about 5%, the added polymer weight should be corrected for moisture (i.e., the added polymer should be 0.9 g on a dry-weight basis). Care is taken to prevent hydrogel-forming absorbent polymer from adhering to the cylinder walls. Piston 636 (minus weight 648) with disc 664 positioned in recess 652 of piston head 650 is inserted into cylinder 634 and positioned on top of the dry hydrogel-forming absorbent polymer 668. If necessary, piston 636 can be turned gently to more-uniformly distribute the hydrogel-forming absorbent polymer on screen 666. Cylinder 634 is the covered with cover 637 and weight 648 is then positioned on end 642 of shaft 638.

A flitted disc (coarse or extra coarse) having a diameter greater than that of cylinder 634 is positioned in a wide/shallow flat-bottomed container that is filled to the top of the fritted disc with Jayco synthetic urine. The piston/cylinder assembly 628 is then positioned on top of this fritted glass disc. Fluid from the container passes through the fritted disc and is absorbed by the hydrogel-forming absorbent polymer 668. As the polymer absorbs fluid, a hydrogel layer is formed in cylinder 634. After a time period of 60 minutes, the thickness of the hydrogel layer is determined. Care is taken that the hydrogel layer does not lose fluid or take in air during this procedure.

The piston/cylinder assembly 628 is then transferred to apparatus 610. The support screen (not shown) and any gap between it and the piston/cylinder assembly 628 is presaturated with saline solution. If the fritted funnel 718 of the PUP apparatus 710 is used to support cylinder 634, the surface of the fritted funnel should be minimally collection relative to the height of the fluid in the collection reservoir, with valves between the fritted funnel and the collection reservoir being in the open position. (The fritted funnel elevation should be sufficient such that fluid passing through the hydrogel layer does not accumulate in the funnel.)

The SFC measurement is initiated by adding NaCl solution through hole 640 in shaft 638 in order to expel air from piston head 650 and then turning stopcock 626 to an open position so that delivery tube 622 delivers fluid to cylinder 634 to a height of 5.0 cm above the bottom of hydrogel layer 668. Although the measurement is considered to have been initiated ($t_o$) at the time NaCl solution is first added, the time at which a stable hydrostatic pressure, corresponding to 5.0 cm of saline solution, and a stable flow rate is attained ($t_s$) is noted. (The time $t_s$ should typically be about one minute or less.) The quantity of fluid passing through hydrogel layer 668 versus time is determined gravimetrically for a time period of 10 minutes. After the elapsed time, piston/cylinder assembly 628 is removed and the thickness of hydrogel layer 668 is measured. Generally the change in thickness of the hydrogel layer is less than about 10%.

In general, flow rate need not be constant. The time-dependent flow rate through the system, $F_s(t)$ is determined, in units of g/sec, by dividing the incremental weight of fluid passing through the system (in grams) by incremental time (in seconds). Only data collected for times between $t_s$ and 10 minutes is used for flow rate calculations. Flow rate results between $t_s$ and 10 minutes is used to calculate a value for $F_s$ (t=0), the initial flow rate through the hydrogel layer. $F_s(t=0)$ is calculated by extrapolating the results of a least-squares fit of $F_s(t)$ versus time to t=0.

For a layer having a very high permeability (e.g., a flow rate greater than ~2 g/sec), it may not be practical to collect fluid for the full 10 minute time period. For flow rates greater than ~2 g/sec, the time of collection can be shortened in proportion to the flow rate.

For some hydrogel-forming absorbent polymers having extremely low permeability, absorption of fluid by the hydrogel competes with transport of fluid through the hydrogel layer and either there is no flow of fluid through the hydrogel layer and into the reservoir or, possibly, there is a net absorption of fluid out of the PUP reservoir. For these extremely low permeability hydrogel layers, it is optional to extend the time for Jayco SynUrine absorption to longer periods (e.g., 16 hours).

In a separate measurement, the flow rate through apparatus 610 and the piston/cylinder assembly 628 ($F_a$) is measured as described above, except that no hydrogel layer is present. If $F_a$ is much greater than the flow rate through the system when the hydrogel layer is present, $F_s$, then no correction for the flow resistance of the SFC apparatus and the piston/cylinder assembly is necessary. In this limit, $F_g = F_s$, where $F_g$ is the contribution of the hydrogel layer to the flow rate of the system. However if this requirement is not satisfied, then the following correction is used to calculate the value of $F_g$ from the values of $F_s$ and $F_a$:

$$F_g = (F_a \times F_s)/(F_a - F_s)$$

The Saline Flow Conductivity (K) of the hydrogel layer is calculated using the following equation:

$$K = \{F_g(t=0) \times L_0\}/\{xAxP\},$$

where $F_g(t=0)$ is the flow rate in g/sec determined from regression analysis of the flow rate results and any correction due to assembly/apparatus flow resistance, $L_0$ is the initial thickness of the hydrogel layer in cm, is the density of the NaCl solution in g/cm$^3$. A is the area of the hydrogel layer in cm$^2$, P is the hydrostatic pressure in dyne/cm$^2$, and the saline flow conductivity, K, is in units of cm$^3$ sec/g.

The average of three determinations should be reported.

3. Ball Burst Strength (BBS) Test

This test determines the ball burst strength(BBS) of an absorbent material at wet state. BBS of an absorbent material is the force (peak load, in grams) required to produce rupture of an absorbent material gel layer that is swollen in Jayco synthetic urine under procedures specified in this test method. BBS of an absorbent material is used for evaluation of the wet integrity of an absorbent material that is swollen in Jayco synthetic urine.

(1) Sampling apparatus

Figure 5:
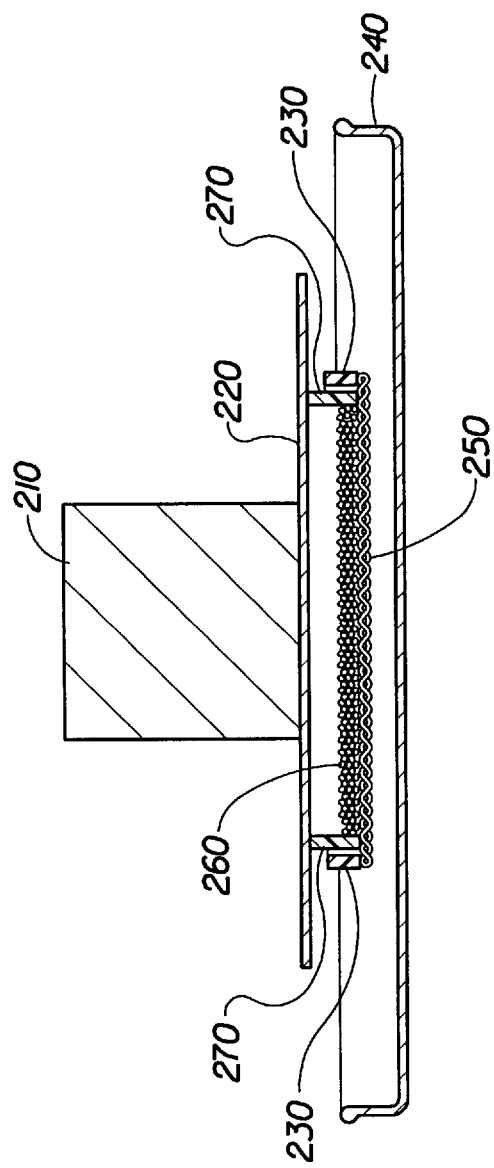
FIG. 5 is a schematic view of an apparatus for measuring the Ball Burst Strength (BBS) value of the absorbent materials.

A suitable sampling apparatus for BBS measurement is shown in FIG. 5. This apparatus comprises an inner-cylinder 270 which is used to contain an absorbent material layer 260, an outside-cylinder 230, a TEFLON flat-bottomed tray 240, an inner-cylinder cover plate 220, and a stainless weight 210. The inner-cylinder 270 is bored from a transparent LEXAN rod (or equivalent, for example Acrylic rod) and has an inner diameter of 6.00 cm (area=28.27 cm$^2$), with a wall thickness of approximately 0.5 cm, and a height of approximately 1.50 cm. The outside-cylinder 230 is bored from a transparent LEXAN rod (or equivalent, for example Acrylic rod) and has an inner diameter that is slightly larger than the outside diameter of the inner-cylinder 270, so that the inner-cylinder 270 fits within the outside-cylinder 230 and slides freely. Outside-cylinder 230 has a wall thickness of approximately 0.5 cm, and a height of approximately 1.00 cm. The bottom of the outside-cylinder 230 is faced with a No. 400 mesh stainless-steel screen 250 that is biaxially stretched to tautness prior to attachment. Inner-cylinder cover plate 220 is made of glass plate with a thickness of 0.8 cm and a weight of 500 g. Stainless weight 210 has a weight of 1700 g.

(2) Burst tester

A Tensile Tester with a burst test load cell (Intelect-II-STD Tensile Tester, made by Thwing-Albert Instrument Co., Pennsylvania) is used for this test. Referring to FIG. 5, this apparatus comprises a circular sample lower clamp platen 280 that is mount on a stationary crosshead 310 provided at the top of a dual screw instrument, a force sensing load cell 330 equipped with a polished stainless steel ball-shaped probe 290, a moving crosshead 320, and a upper clamping platen 300 that is used to clamp a sample 260 pneumatically. Lower clamp platen 280 is mount on the stationary crosshead 310. The force sensing load cell 330 is equipped with the probe 290. Both lower clamp platen 280 and upper clamp platen 300 have a diameter of 115 mm, a thickness of 2.9 mm, and a circular opening 18.65 mm in diameter. Polished stainless steel ball-shaped probe 290 has a diameter of 15.84 mm. The moving crosshead 320 moves up, causing the probe 290 to contact and penetrate the sample 260. When the probe 290 penetrate the sample 260, the test is considered complete, and the test result data are displayed and recorded.

(3) Procedure

Referring to FIG. 5, inner-cylinder 270 is inserted into outside-cylinder 230. 1.4 g aliquot of an absorbent material is added to the inner-cylinder 270 and dispersed evenly on the 400 mesh stainless screen 250 of the bottom via gently shaking and/or tapping of the assembled cylinders. The assembled cylinders with absorbent material are transferred to TEFLON flat-bottomed tray 240, and inner-cylinder cover plate 220 is positioned onto inner-cylinder 270. 42.0 Milliliters of Jayco synthetic urine is applied to TEFLON flat-bottomed tray 240. Jayco synthetic urine from TEFLON flat-bottomed tray 240 passes through the stainless screen 250. All of the applied urine is absorbed by the absorbent material 260 for 5 minutes. Then the stainless weight 210 is placed onto the inner-cylinder cover plate 220. After further 25 minutes, stainless weight 210 and inner-cylinder cover plate 220 are removed. Consequently, the predetermined layer 260 of the swollen absorbent material for the GBD measurement has been prepared. The inner-cylinder 270 with the absorbent material gel layer 260 is immediately transferred to the Burst Tester for BBS test.

Figure 6:
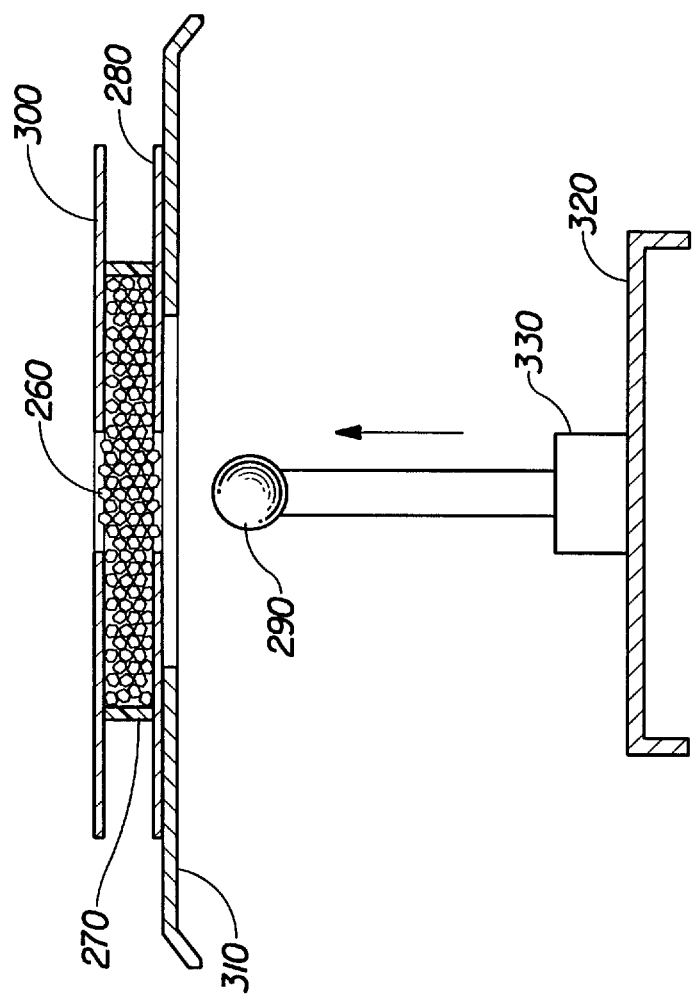
FIG. 6 is a schematic view of an apparatus for preparing a predetermined layer of the swollen absorbent materials.

Referring to FIG. 6, inner-cylinder 270 with an absorbent material gel layer 260 is positioned on lower clamp platen 280 and is fixed pneumatically with upper clamping platen 300. Using a break sensitivity of 10.00 g and a test speed of 5.00 inch/minutes and Initiating the test by pressing the Test switch. The moving crosshead 320 moves up until polished stainless steel ball-shaped probe 290 penetrate absorbent material gel layer 260. After a sample burst is registered, moving crosshead 320 returns to start position. The BBS is expressed as peak load grams. The average of three determinations should be reported.

4. Compression Recovery (CR) Test

This test determines the recovery from compression of an absorbent material that is swollen in Jayco synthetic urine. Recovery of compression (RC) is the extent that an absorbent material at wet state has returned to its original shape when subjected to the compression under procedures specified in this test method. RC of an absorbent material is used for evaluation of the wet integrity of an absorbent material that is swollen in Jayco synthetic urine, and is related to the ability of an absorbent material at wet state to resume its original shape after being subjected to tensional and torsional forces of varying intensity and direction during normal use. RC is also related to the tightness or snugness of an absorbent material at wet state.

(1) Sampling apparatus

A suitable sampling apparatus for RC measurement is similar to the apparatus used in the BBS test (as shown in FIG. 5) but is higher in height than the latter. The apparatus for RC measurement comprises an inner-cylinder 270 which is used to contain an absorbent material layer 260, an outside-cylinder 230, a TEFLON f flat-bottomed tray 240, an inner-cylinder cover plate 220, and a stainless weight 210. The inner-cylinder 270 is bored from a transparent LEXAN rod (or equivalent, for example Acrylic rod) and has an inner diameter of 6.00 cm (area=28.27 cm$^2$), with a wall thickness of approximately 0.5 cm, and a height of approximately 2.00 cm. The outside-cylinder 230 is bored from a transparent LEXAN rod (or equivalent, for example Acrylic rod) and has an inner diameter that is slightly larger than the outside diameter of the inner-cylinder 270, so that the inner-cylinder 270 fits within the outside-cylinder 230 and slides freely. Outside-cylinder 230 has a wall thickness of approximately 0.5 cm, and a height of approximately 1.00 cm. The bottom of the outside-cylinder 230 is faced with a No. 400 mesh stainless-steel screen 250 that is biaxially stretched prior to attachment. Inner-cylinder cover plate 220 is made of glass plate with a thickness of 8.00 cm and a weight of 530 g. Stainless weight 210 has a weight of 1672 g.

(2) Compression Tester

A Handy-type Compression Tester (KES-G5, made by Kato Tech Co., Ltd., Kyoto) is used in this method. Referring to FIG. 7, the mechanical part of this apparatus comprises a compression plate 310, a load indicator 350 that is connected to compression plate 310, a drive mechanism 360, and a specimen stand 320. A load indicator 350 is capable of showing the total load (gf/cm$^2$) carried by the test specimen. A compression plate 310 is circular plate with a area of 2.00 cm$^2$, a thickness of 0.40 cm. A driving mechanism 360 is capable of imparting to the compression plate 310 a uniform and steady controlled compression/recovery rate (cm/sec.).

(3) Procedure

Inner-cylinder 270 is inserted into outside-cylinder 230. 2.8 g aliquot of an absorbent material is added to the inner-cylinder 270 and dispersed evenly on the 400 mesh stainless screen 250 of the bottom via gently shaking and/or tapping of the assembled cylinders. The assembled cylinders with absorbent material are transferred to TEFLON flat-bottomed tray 240, and inner-cylinder cover plate 220 is positioned onto inner-cylinder 270. 56 Milliliters of Jayco synthetic urine is added to TEFLON flat-bottomed tray 240. Jayco synthetic urine from TEFLON flat-bottomed tray 240 passes through the stainless screen 250. All of the applied urine is absorbed by the absorbent material 260 for 5 minutes. Then the stainless weight 210 is placed onto the inner-cylinder cover plate 220. After further 25 minutes, stainless weight 210 and inner-cylinder cover plate 220 are removed. Consequently, the predetermined layer 260 of the swollen absorbent material for the GBD measurement has been prepared. The inner-cylinder 270 with the absorbent material gel layer 260 is immediately transferred to the Compression Tester for RC test.

Figure 8:
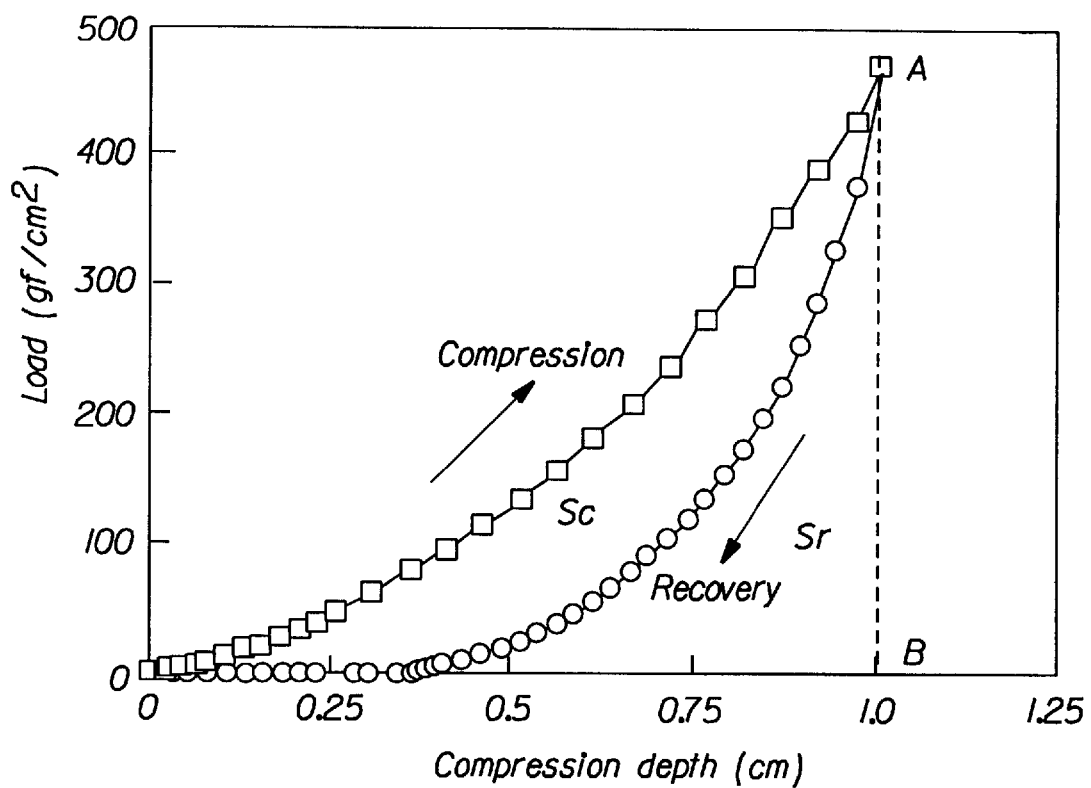
FIG. 8 is a graph showing the relationship between the compression/recovery load and the compression depth in the CR test.

Inner-cylinder 270 with an absorbent material gel layer 260 is immediately positioned on specimen stand 320 of the Handy-type Compression Tester as shown in FIG. 7. Compression plate 310 is positioned on to absorbent material gel layer 330 surface but without compressing the specimen (0 gf/cm$^2$ load at 0 cm compression depth). The compression depth is selected in the range from 0 to 1.00 cm, the compression/recovery rate is selected at 0.01 cm/sec, and the load sensitivity is selected at 10 gf. Start the test by pushing start switch of the Tester. Drive mechanism 360 drives compression plate 310 to compress an absorbent material gel layer 330 at a speed of 0.01 cm/sec. till the compression depth reaches 1.00 cm, and then the compression plate 310 returns at the same speed as compression to the original position. The load (gf/cm$^2$) and depth (cm) are recorded by using a XY-Recorder. Compression recovery (CR) is expressed as the percentage of recovery work (gfcm/cm$^2$) to compression work (gfcm/cm$^2$). As shown in FIG. 8, recovery work corresponds to the area (Sr) that is enclosed by the recovery curve, AB line and horizontal axis. Compression work corresponds to the area that is enclosed by the compression curve, AB line and horizontal axis, and is equal to the total area of Sc+Sr, where Sc corresponds to the area that is enclosed by the compression curve, and the recovery curve. Therefore, RC can be calculated from the following equation:

$$RC\% = Sr/(Sc+Sr) \times 100,$$

The average of three determinations should be reported.

5. Gel Volume

Gel volume of a hydrogel-forming absorbent polymer is defined as its free-swell absorbent capacity when swollen in an excess of Jayco synthetic urine. It provides a measure of the maximum absorbent capacity of the polymer under conditions of use where the pressures on the polymer are relatively low. For most hydrogel-forming absorbent polymers, gel volume is determined by the method described in U.S. Reissue Pat. No. 32,649 (Brandt et al), reissued Apr. 19, 1988 (herein incorporated by reference) but using the Jayco Synthetic Urine described above. All of the chemicals are of reagent grade. The pH of the synthetic urine is in the range of 6.0 to 6.4. The gel volume is calculated on a dry-weight basis. The dry weight used in the gel volume calculation is determined by oven drying the hydrogel-forming absorbent polymer at 105° C. for three hours.

6. Extractable Component

The percentage of extractable polymer in carboxylic acid based hydrogel-forming polymers is determined by the Extractable Polymer Content Determination—Carboxylic Acid Based Hydrogel-Forming Polymers method described in U.S. Reissue Pat. No. 32,649 (Brandt et al), reissued Apr. 19, 1988 (herein incorporated by reference), but using 0.9% saline solution, filtering the supernatant through a Whatman 0.7 micron GF/F glass microfiber filter (e.g., Catalog #1825-125) or equivalent, and calculating the extractable polymer on a dry-weight basis. It is also noted that in U.S. Reissue Pat. No. 32,649 that $V_a$ should refer to the volume of base and $V_b$ should refer to the volume of acid.

G. Examples of Absorbent Materials

PRECURSOR PARTICLE EXAMPLE

An aqueous monomer solution is prepared consisting of 4000 g of partially neutralized acrylic acid having a 75 mol % portion thereof neutralized with caustic soda, 3.7 g of N,N'-methylene-bis-acrylamide, and 6000 g of water. The aqueous monomer solution is fed into the reaction vessel, which is subsequently purged with nitrogen gas to remove the remaining entrapped air from the reaction system. Then, the mixture was stirred and heated to about 45° C., and a solution of 20 g of 2,2'-azo-bis-(2-amidinopropane)-dihydrochloride in 100 g of water is added thereto as a polymerization initiator. Polymerization begins about 15 minutes after the addition of the polymerization initiator. With the progress of the polymerization, the aqueous monomer solution gives rise to a soft water-containing gel. The inner temperature of the reaction system is kept at 80°–90° C. for hours to further complete the polymerization. A swollen absorbent gelling polymer is formed. The resultant swollen absorbent gelling polymer thus obtained is spread on a standard #50 size metal gauge and dried with a hot air at 150° C. The dried particles are pulverized with a hammer type crusher and sifted with a standard #20 sieve (850 microns) to obtain particles that pass through the standard #20 sieve. As a result, dry white precursor absorbent gelling particles are obtained.

EXAMPLE 1

A solution is prepared consisting of 250 g of polyallyamine solution with a concentration of 10% by weight (PAA-C, supplied from Nitto Boseki Co. Ltd., Tokyo), 1600 g of ethanol. The solution is applied to 2500 g of the precursor particles made in accordance with the Precursor Particle Example in a 20-liters evaporator flask. The precursor particles have a particle size such that the precursor particles pass through a standard #20 sieve (850 microns) and are retained on a standard #100 sieve (150 microns). The mixture is thoroughly mixed with a spatula until all of the precursor particles are wetted with the above solution. The solvent included in the resultant mixture is evaporated with a rotary evaporator (EYELA N-11 type, available from TOKYO RIKAKIKAI CO., LTD., Tokyo) at 60° C. The resultant product is vacuum dried at 100° C. for 3 hours. The dried absorbent material is pulverized with a hammer type crusher and sifted with a standard #20 sieve (850 microns) to obtain particles that pass through the standard #20 sieve. As a result, dry white particles of the resultant absorbent material (Ex. #1) are obtained. In comparison of the properties of the precursor particles and the absorbent material (Ex. #1), the gel volume, BBS value and RC value of the precursor particles are 40.0 g/g, 17 gf and 9%, respectively, while the gel volume, BBS value and RC value of the absorbent material (Ex. #1) are 39.2 g/g, 160 gf and 62%, respectively.

EXAMPLE 2

Figure 9:
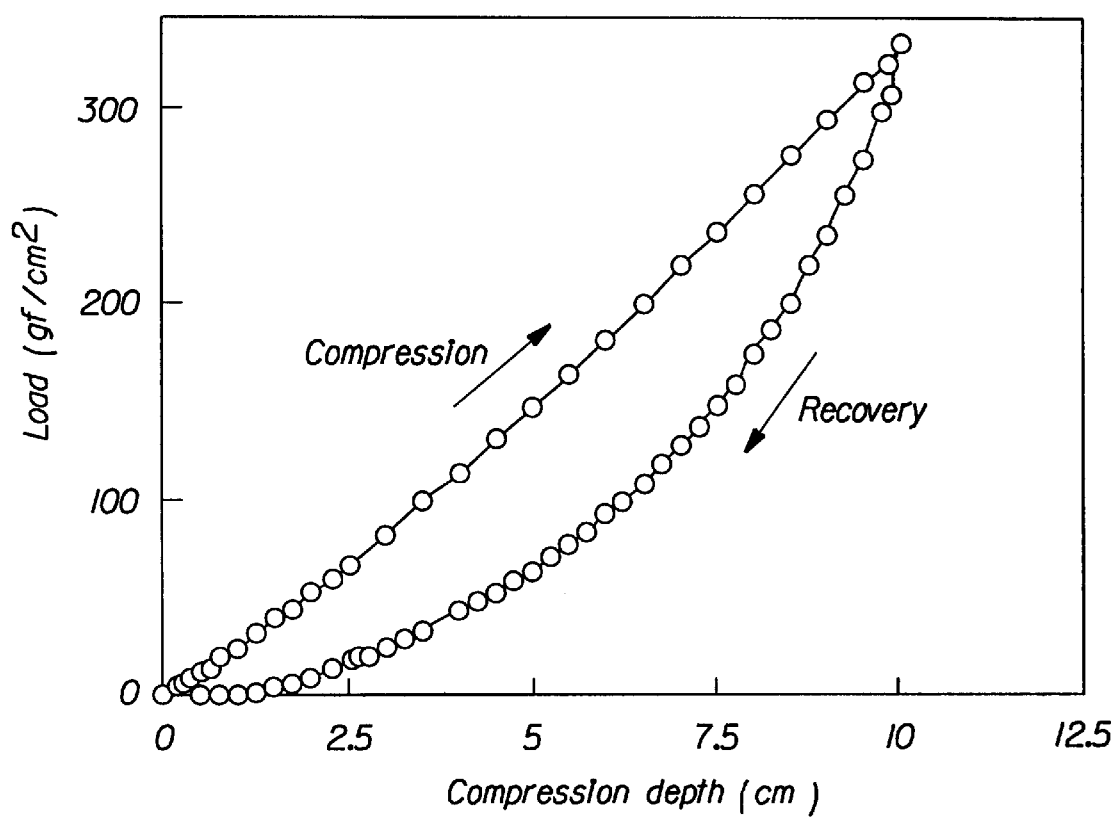
FIG. 9 is a graph showing one example of the relationship between the compression/recovery load and the compression depth in the CR test.
Figure 10:
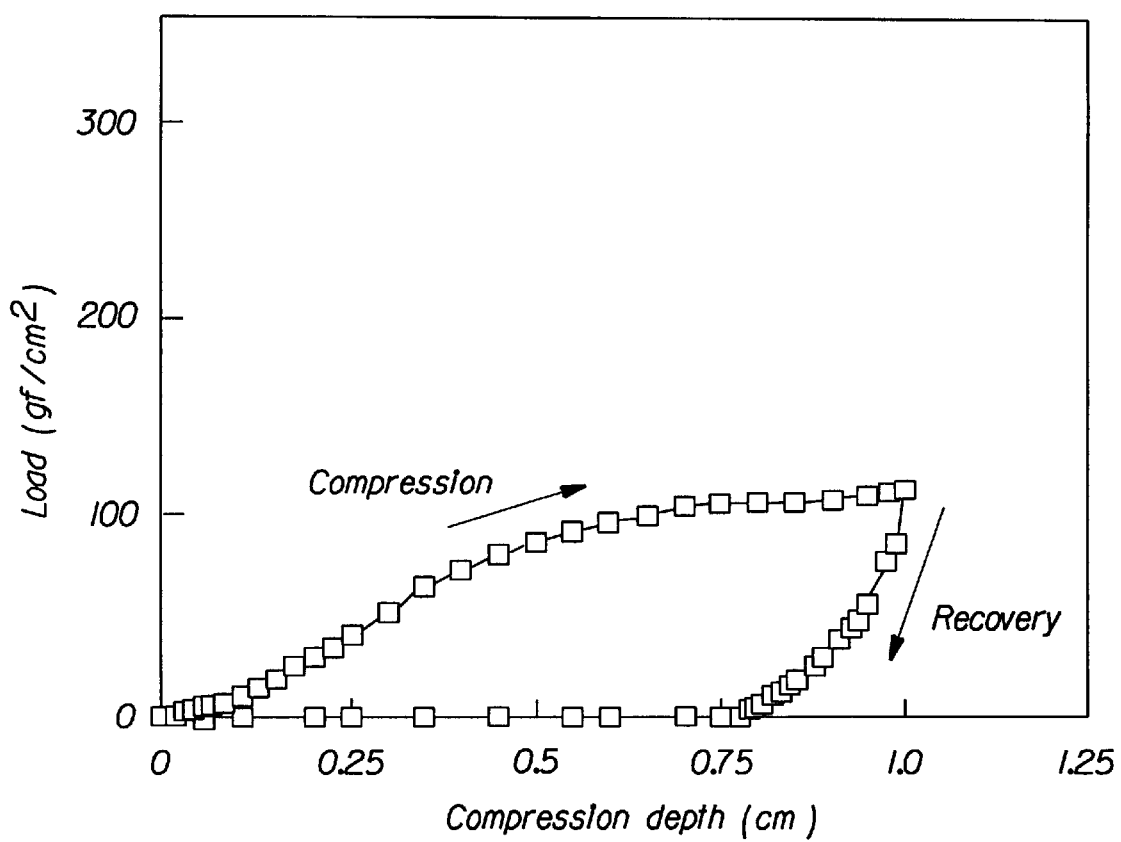
FIG. 10 is a graph showing a comparison example of the relationship between the compression/recovery load and the compression depth in the CR test.

Absorbent gelling particles obtained from commercial sources are used in this example. 2500 Grams of Aqualic CA L761f (lot #4N22-029) supplied from Nippon Shokubai Co. Ltd., Osaka, Japan, is placed in a 20-liters rotary evaporator flask. L761f is a surface-crosslinked absorbent gelling particle. A solution consisting of 250 g of polyallyamine solution with a concentration of 10% by weight (PAA-C, supplied from Nitto Boseki Co. Ltd., Tokyo), 1600 g of ethanol is applied to the flask. The mixture is thoroughly mixed with a spatula until all of the precursor particles are wetted with the above solution. The solvent included in the resultant mixture is evaporated with a rotary evaporator (EYELA N-11 type, available from TOKYO RIKAKIKAI CO., LTD., Tokyo) at 60° C. The resultant product is vacuum dried at 100° C. for 3 hours. The dried absorbent material is pulverized with a hammer type crusher and sifted with a standard #20 sieve (850 microns) to obtain particles that pass through the standard #20 sieve. As a result, dry white particles of the resultant absorbent material (Ex. #2) are obtained. The CR curve for the absorbent material (Ex. #2) is shown in FIG. 9. By contrast, the CR curve for L761f is shown in FIG. 10. A comparison table for showing the properties of these materials is summarized in Table 1 below:

TABLE 1

| Sample | Gel volume (g/g) | GBD (g/cm$^3$) | SFC (10$^{-7}$ cm$^3$ sec/g) | BBS (gf) | CR (%) | Extractable component (%) |
|---|---|---|---|---|---|---|
| L76lf | 37.5 | 1.09 | 4 | 17 | 7 | 12.3 |
| Ex. #2 | 36.2 | 0.75 | 29.8 | 138 | 51 | 8.9 |

EXAMPLE 3

Absorbent gelling particles obtained from commercial sources are used in this example. 100 Grams of Aqualic CA L761f (lot #4E28-012) supplied from Nippon Shokubai Co. Ltd., Osaka, Japan, is placed in a Kitchen-type Mixer. A solution is prepared consisting of 10 g of polyallyamine solution with a concentration of 10% by weight (PAA-C, supplied from Nitto Boseki Co. Ltd. Osaka), and 20 g of ethanol. After a portion of the solution is sprayed onto the absorbent gelling particles with a sprayer (type: 24-182-04; available from Iuchi Seieido Co., Ltd., Osaka), the mixer is operated for a period of about 4 minutes. Then more solution is sprayed, and the mixer is operated again for another 4 minutes. Repeating the spraying/mixing processes till all the solution are sprayed on to the absorbent gelling particle. The resultant mixture is dried with an vacuum oven at about 100° C. for about 3 hours. The dried particles are pulverized with a hammer type crusher and sifted with a standard #20 sieve (850 microns) to obtain particles that pass through the standard #20 sieve. As a result, dry white particles of the resultant absorbent material are obtained. The properties of the resultant absorbent material (Ex. #3) are shown in Table 2.

TABLE 2

| Sample | Gel volume (g/g) | GBD (g/cm$^3$) | SFC (10$^{-7}$ cm$^3$ sec/g) | BBS (gf) | CR (%) | Extractable weight (%) |
|---|---|---|---|---|---|---|
| L76lf | 36.4 | 1.07 | 9 | 21 | 8 | 11.1 |
| Ex. #3 | 35.0 | 0.78 | 45 | 124 | 55 | 9.0 |

What is claimed is:

1. An absorbent article comprising: (a) a liquid pervious topsheet; (b) a liquid impervious backsheet; and (c) an absorbent core positioned between said topsheet and said backsheet, wherein said absorbent core comprises an absorbent member comprising at least one region which comprises an absorbent material, wherein said absorbent material comprises a mixture of (1) a plurality of absorbent gelling particles comprising a water-insoluble, water-swellable polymer, and (2) an absorbent property modification polymer reactive with at least one component included in a urine, wherein said plurality of absorbent gelling particles are spontaneously connective through said absorbent property modification polymer in response to an application of urine, and wherein when said absorbent material swells by absorbing a urine and is formed into a predetermined layer of the swollen absorbent material under a predetermined load, said layer of the swollen absorbent material has a Gel Bulk Density (GBD) value of below 0.95 g/cm$^3$ in the GBD test.

2. The absorbent article according to claim 1 wherein said absorbent material is in a concentration of from about 60 to 100%, by weight of said at least one region of said absorbent member.

3. The absorbent article according to claim 1 wherein said absorbent property modification polymer is a cationic polymer.

4. The absorbent article according to claim 1 wherein said absorbent property modification polymer is cationic, and said polymer is reactive with at least one urine component that is an anion having at least two ionic charge numbers.

5. The absorbent article according to claim 4, wherein said cationic polymer is reactive with a phosphate ion, sulfate ion, or carbonate ion in a urine.

6. The absorbent article according to claim 3 wherein said cationic polymer is a polyamine or polyimine material.

7. The absorbent article according to claim 6 wherein said polyamine is selected from the group consisting of (a) polymers having primary amine groups; (b) polymers having secondary amine groups; (c) polymers having tertiary amine groups; and (d) mixtures thereof.

8. An absorbent article comprising: (a) a liquid pervious topsheet; (b) a liquid impervious backsheet; and (c) an absorbent core positioned between said topsheet and said backsheet, wherein said absorbent core comprises an absorbent member comprising at least one region which comprises an absorbent material, wherein said absorbent material comprises a mixture of (1) a plurality of absorbent gelling particles comprising a water-insoluble, water-swellable polymer, and (2) an absorbent property modification polymer reactive with at least one component included in a urine, wherein said plurality of absorbent gelling particles are spontaneously connective through said absorbent property modification polymer in response to an application of urine, and wherein when said absorbent material swells by absorbing a urine and is formed into a predetermined layer of the swollen absorbent material, said layer of the swollen absorbent material has a Saline Flow Conductivity (SFC) value of at least $20 \times 10^{-7}$ cm$^3$ sec/g in the SFC test.

9. The absorbent article according to claim 8 wherein said absorbent material is in a concentration of from about 60 to 100%, by weight of said at least one region of said absorbent member.

10. The absorbent article according to claim 8 wherein said absorbent property modification polymer is a cationic polymer.

11. The absorbent article according to claim 8 wherein said absorbent property modification polymer is cationic, and said polymer is reactive with at least one urine component that is an anion having at least two ionic charge numbers.

12. The absorbent article according to claim 11, wherein said cationic polymer is reactive with a phosphate ion, sulfate ion, or carbonate ion in a urine.

13. The absorbent article according to claim 10 wherein said cationic polymer is a polyamine or polyimine material.

14. The absorbent article according to claim 13 wherein said polyamine is selected from the group consisting of (a) polymers having primary amine groups; (b) polymers having secondary amine groups; (c) polymers having tertiary amine groups; and (d) mixtures thereof.

15. An absorbent article comprising: (a) a liquid pervious topsheet; (b) a liquid impervious backsheet; and (c) an absorbent core positioned between said topsheet and said backsheet, wherein said absorbent core comprises an absorbent member comprising at least one region which comprises an absorbent material, wherein said absorbent material comprises a mixture of (1) a plurality of absorbent gelling particles comprising a water-insoluble, water-swellable polymer, and (2) an absorbent property modification polymer reactive with at least one component included in a urine, wherein said plurality of absorbent gelling particles are spontaneously connective through said absorbent property modification polymer in response to an application of urine, and wherein when said absorbent material swells by absorbing a urine and is formed into a predetermined layer of the swollen absorbent material, said layer of the swollen absorbent material has a Ball Burst Strength (BBS) value of at least 30 gf in the test.

16. The absorbent article according to claim 15 wherein said absorbent material is in a concentration of from about 60 to 100%, by weight of said at least one region of said absorbent member.

17. The absorbent article according to claim 15 wherein said absorbent property modification polymer is a cationic polymer.

18. The absorbent article according to claim 15 wherein said absorbent property modification polymer is cationic, and said polymer is reactive with at least one urine component that is an anion having at least two ionic charge numbers.

19. The absorbent article according to claim 18, wherein said cationic polymer is reactive with a phosphate ion, sulfate ion, or carbonate ion in a urine.

20. The absorbent article according to claim 17 wherein said cationic polymer is a polyaniline or polyimine material.

21. The absorbent article according to claim 20 wherein said polyamine is selected from the group consisting of (a) polymers having primary amine groups; (b) polymers having secondary amine groups; (c) polymers having tertiary amine groups; and (d) mixtures thereof.

22. An absorbent article comprising: (a) a liquid pervious topsheet; (b) a liquid impervious backsheet; and (c) an absorbent core positioned between said topsheet and said backsheet, wherein said absorbent core comprises an absorbent member comprising at least one region which comprises an absorbent material, wherein said absorbent material comprises a mixture of (1) a plurality of absorbent gelling particles comprising a water-insoluble, water-swellable polymer, and (2) an absorbent property modification polymer reactive with at least one component included in a urine, wherein said plurality of absorbent gelling particles are spontaneously connective through said absorbent property modification polymer in response to an application of urine, and wherein when said absorbent material swells by absorbing a urine and is formed into a predetermined layer of the swollen absorbent material, said layer of the swollen absorbent material has a Compression Recovery (CR) value of at least 15% in the CR test.

23. The absorbent article according to claim 22 wherein said absorbent material is in a concentration of from about 60 to 100%, by weight of said at least one region of said absorbent member.

24. The absorbent article according to claim 22 wherein said absorbent property modification polymer is a cationic polymer.

25. The absorbent article according to claim 22 wherein said absorbent property modification polymer is cationic, and said polymer is reactive with at least one urine component that is an anion having at least two ionic charge numbers.

26. The absorbent article according to claim 25, wherein said cationic polymer is reactive with a phosphate ion, sulfate ion, or carbonate ion in a urine.

27. The absorbent article according to claim 24 wherein said cationic polymer is a polyamine or polyimine material.

28. The absorbent article according to claim 27 wherein said polyamine is selected from the group consisting of (a) polymers having primary amine groups; (b) polymers having secondary amine groups; (c) polymers having tertiary amine groups; and (d) mixtures thereof.

* * * * *

UNITED STATES PATENT AND TRADEMARK OFFICE
CERTIFICATE OF CORRECTION

PATENT NO. : 5,858,535
DATED : January 12, 1999
INVENTOR(S) : Lin Wang et al.

Page 1 of 1

It is certified that error appears in the above-identified patent and that said Letters Patent is hereby corrected as shown below:

Column 9,
Line 35, delete "substances" and insert -- substance --.

Column 12,
Line 38, delete "arines" and insert -- amines --.

Column 19,
Line 43, delete "Chattedjee" and insert -- Chatterjee --.

Column 22,
Line 12, delete "flitted" and insert -- fritted --.
Line 29, delete "collection" and insert -- elevated --.

Column 30,
Line 21, delete "polyaniline" and insert -- polyamine --.

Signed and Sealed this

Seventh Day of February, 2006

JON W. DUDAS
*Director of the United States Patent and Trademark Office*